US008372527B2

(12) United States Patent
Morishita et al.

(10) Patent No.: US 8,372,527 B2
(45) Date of Patent: Feb. 12, 2013

(54) MATERIAL FOR ORGANIC ELECTROLUMINESCENT ELEMENT, AND ORGANIC ELECTROLUMINESCENT ELEMENT

(75) Inventors: Hironobu Morishita, Sodegaura (JP); Yuichiro Kawamura, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 422 days.

(21) Appl. No.: 12/668,337

(22) PCT Filed: Jun. 30, 2008

(86) PCT No.: PCT/JP2008/061815
§ 371 (c)(1),
(2), (4) Date: Jan. 8, 2010

(87) PCT Pub. No.: WO2009/008277
PCT Pub. Date: Jan. 15, 2009

(65) Prior Publication Data
US 2010/0187519 A1 Jul. 29, 2010

(30) Foreign Application Priority Data
Jul. 11, 2007 (JP) .................. 2007-182590

(51) Int. Cl.
*H01L 51/54* (2006.01)
*C07D 487/22* (2006.01)
*C07D 471/22* (2006.01)
*C07D 487/04* (2006.01)

(52) U.S. Cl. ........ 428/690; 428/917; 313/504; 313/506; 546/27; 546/41; 548/301.7; 548/302.4

(58) Field of Classification Search ........................ None
See application file for complete search history.

(56) References Cited

U.S. PATENT DOCUMENTS

| 4,983,741 | A | | 1/1991 | Katayama et al. | |
|---|---|---|---|---|---|
| 5,998,803 | A | * | 12/1999 | Forrest et al. | ................. 257/40 |
| 6,423,429 | B2 | | 7/2002 | Kido et al. | |
| 6,566,807 | B1 | | 5/2003 | Fujita et al. | |
| 2003/0006411 | A1 | | 1/2003 | Kido et al. | |
| 2004/0062949 | A1 | | 4/2004 | Pfeiffer et al. | |
| 2004/0131882 | A1 | * | 7/2004 | Matsuura et al. | ............. 428/690 |
| 2005/0255334 | A1 | | 11/2005 | Kang et al. | |
| 2007/0160871 | A1 | * | 7/2007 | Morishita et al. | ............. 428/690 |

FOREIGN PATENT DOCUMENTS

| CN | 101139351 A | * | 3/2008 |
|---|---|---|---|
| EP | 0320201 | | 6/1989 |
| JP | 01-149787 A | | 6/1989 |
| JP | 04-297076 A | | 10/1992 |
| JP | 05-249718 A | | 9/1993 |
| JP | 05-308145 A | | 11/1993 |
| JP | 11-251067 A | | 9/1999 |
| JP | 2000-196140 A | | 7/2000 |
| JP | 2000-208263 A | | 7/2000 |
| JP | 2001-297883 A | | 10/2001 |
| JP | 2003-031365 A | | 1/2003 |
| JP | 2004-514257 A1 | | 5/2004 |
| JP | 2005-033185 A | | 2/2005 |
| WO | 2006078193 A1 | | 7/2006 |

OTHER PUBLICATIONS

Translation for JP 2005-033185, which was published Feb. 2005.*
Translation for JP 2000-208263, which was published Jul. 2000.*
Machine translation for CN 101139351 A (Mar. 2008).*
Korshak, V. V. et al. Two-stage synthesis of aroylenebenzimidazoles, Izvestiya Akademii Nauk SSSR, Seriya Khimicheskaya, 1978, No. 2, p. 422-426.
Manukian, B. K., Pyromellitic acid and cumidinic acid derivatives. XIV. Imidazoles from pyromellitic acid dianhydride, Helvetica Chimica Acta, 1969, vol. 52, No. 7, p. 2143-2150.
Korshak, V. V., Interaction of aroylenebenzimidazoles with nucleophilic reagents, Khimiya Geterotsiklicheskikh Soedinenii, 1972, No. 2, p. 247-252.
Arient, J. et al., Imidazole dyes. XV. Synthesis of aroyleneimidazole dyes and influence of substitution on their dyeing properties, Collection of Czechoslovak Chemical Communications, 1965, vol. 30, No. 11, p. 3718-3729.

* cited by examiner

*Primary Examiner* — Dawn L. Garrett
(74) *Attorney, Agent, or Firm* — Foley & Lardner LLP

(57) ABSTRACT

A material for an organic electroluminescence device including at least one of compounds shown by the following formula (Ia), (Ib), (IIa), (IIb), (III), (IVa) or (IVb):

(Ia)

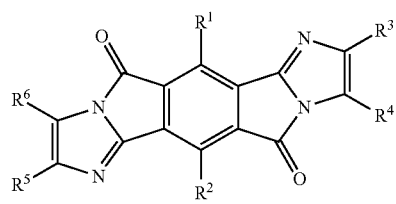

(Ib)

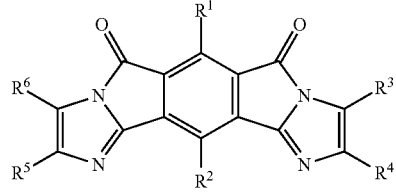

(IIa)

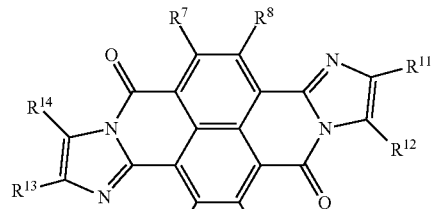

(IIb)

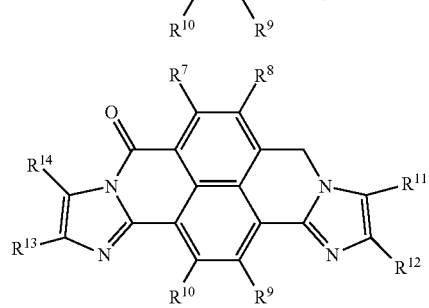

(III)

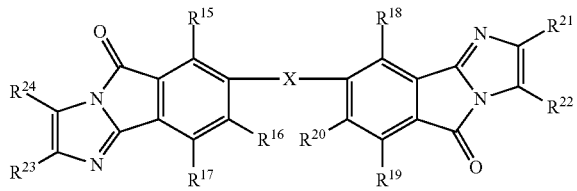

(IVa)

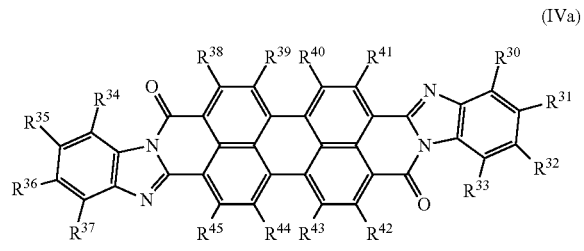

(IVb)

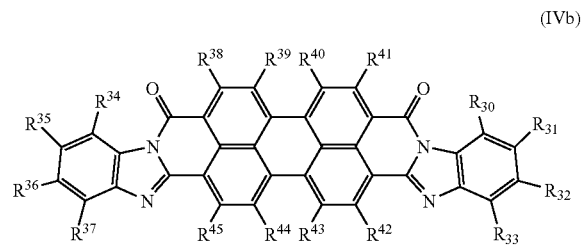

3 Claims, 1 Drawing Sheet

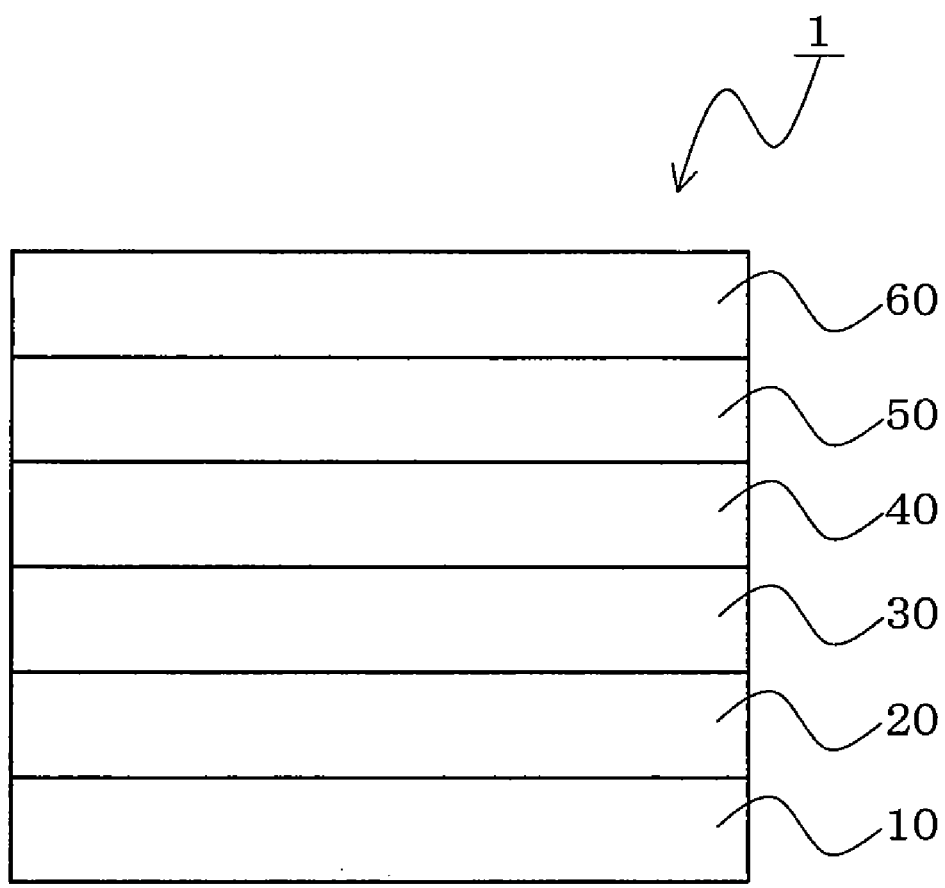

MATERIAL FOR ORGANIC ELECTROLUMINESCENT ELEMENT, AND ORGANIC ELECTROLUMINESCENT ELEMENT

CROSS-REFERENCE TO PRIOR APPLICATION

This is the U.S. National Phase Application under 35 U.S.C. §371 of International Patent Application No. PCT/JP2008/061815 filed Jun. 30, 2008, which claims the benefit of Japanese Patent Application No. 2007-182590 filed Jul. 11, 2007, both of which are entirely incorporated by reference herein. The International Application was published in Japanese on Jan. 15, 2009 as WO2009/008277 under PCT Article 21(2).

TECHNICAL FIELD

The invention relates to a material for an organic electroluminescence device and an organic electroluminescence device using the same.

BACKGROUND ART

An organic electroluminescence device (hereinafter the term "electroluminescence" is often abbreviated as "EL") is a self-emission device utilizing the principle that a fluorescent material emits light by the recombination energy of holes injected from an anode and electrons injected from a cathode when an electric field is impressed.

Since C. W. Tang et al. of Eastman Kodak Co. reported a low-voltage driven organic EL device in the form of a stacked type device, studies on organic EL devices wherein organic materials are used as the constituent materials have actively been conducted.

The organic EL device reported by Tang et al. has a stacked structure in which tris(8-hydroxyquinolinol)aluminum is used as an emitting layer and a triphenyldiamine derivative is used as a hole-transporting layer. The advantages of the stack structure are to increase injection efficiency of holes to the emitting layer, to increase generation efficiency of excitons generated by recombination by blocking electrons injected from the cathode, to confine the generated excitons in the emitting layer, and so on.

As the stacked structure of the organic EL device, a two-layered type of a hole-transporting (injecting) layer and an electron-transporting emitting layer, and a three-layered type of a hole-transporting (injecting) layer, an emitting layer and an electron-transporting (injecting) layer are widely known. In such stack structure devices, their device structures and fabrication methods have been contrived to increase recombination efficiency of injected holes and electrons.

As a hole-transporting material used in an organic EL device, an aromatic diamine derivative or an aromatic fused ring diamine derivative has heretofore been known.

However, in order to obtain a sufficient luminance by an organic EL device using these aromatic diamine derivatives as the hole-transporting material, a higher voltage is required to be applied. As a result, problems occur such as a shortened device life or an increased consumption power.

In order to solve these problems, doping a hole-injecting layer of an organic EL device with an electron-accepting compound such as Lewis acid or using an electron-accepting compound singly as an injecting layer has been proposed (Patent Documents 1 to 7, or the like). However, an electron-accepting compound used in Patent Documents 1 to 4 has defects that they are unstable to be handled in the production process of an organic EL device or they cause the life of an organic EL device to be shortened due to insufficiency in stability such as heat resistance when an organic EL device is driven.

In addition, tetrafluoro-tetracyanoquinodimethane (TC-NQF$_4$) which is an electron-accepting compound exemplified in Patent Documents 3, 5 to 7 or the like has a small molecular weight and substituted by fluorine. Due to a high sublimation property, it may diffuse within an apparatus when fabricating an organic EL device by vacuum vapor deposition, thereby to contaminate the apparatus or the device.

Patent Document 1: JP-A-2003-031365
Patent Document 2: JP-A-2001-297883
Patent Document 3: JP-A-2000-196140
Patent Document 4: JP-A-H11-251067
Patent Document 5: JP-A-H04-297076
Patent Document 6: JP-T-2004-514257
Patent Document 7: US2005/0255334A1

The invention has been made in view of the above-mentioned problems, and the object thereof is to provide an electron-accepting material which is preferable as a constituting material of an organic EL device.

DISCLOSURE OF THE INVENTION

As a result of intensive studies, the inventors noticed a compound of the invention which can be obtained by reacting a tetracarboxylic anhydride derivative and a diamine compound. These compounds maintain a planar molecular structure and therefore are thermally stable. In addition, due to the presence of the following structural unit in the molecule, these compounds have a higher degree of electron acceptability. Further, by introducing a specific substituent, it is possible to further enhance electron acceptability or to cause crystalline property to be changed.

For example, the U.S. Pat. No. 5,077,142 discloses unsubstituted perylenetetracarboxylic acid benzimidazole as an electron-transporting material of an organic EL device. However, unsubstituted perylenetetracarboxylic acid benzimidazole has problems that the solubility is low, the deposition temperature is high, or the like. The inventors have found that, by introducing a fluorine atom or the like to this compound, solubility or deposition temperature can be improved, and further, electron acceptability can be improved.

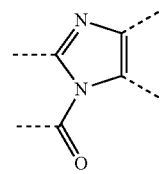

The inventors have found that, by applying the compound of the invention having these characteristics to an organic EL device, in particular, to a hole-injecting layer, a lower driving voltage or a prolonged device life can be realized.

According to the invention, the following material for an organic EL device or the like can be provided.

1. A material for an organic electroluminescence device comprising at least one of compounds shown by the following formula (Ia) or (Ib):

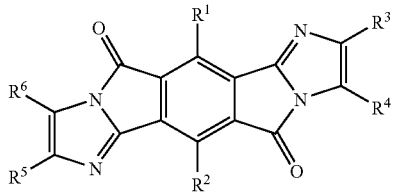

(Ia)

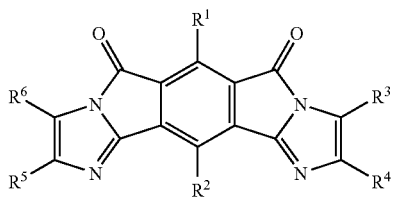

(Ib)

wherein $R^1$ to $R^6$, which may be the same or different, are a hydrogen atom, a halogen atom, a cyano group, an alkyl group, an aryl group, a fluoroalkyl group, an alkoxy group, an aryloxy group or a heterocyclic ring; and adjacent groups of $R^1$ to $R^6$ may be bonded to form an aromatic ring or a heterocyclic ring, and the aromatic ring or the heterocyclic ring may have a substituent.

2. A material for an organic electroluminescence device comprising at least one of compounds shown by the following formula (IIa) or (IIb):

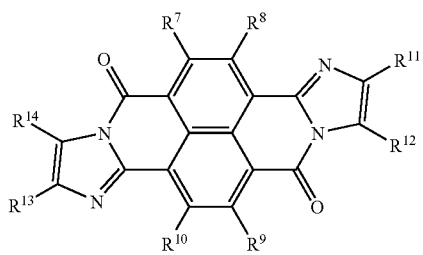

(IIa)

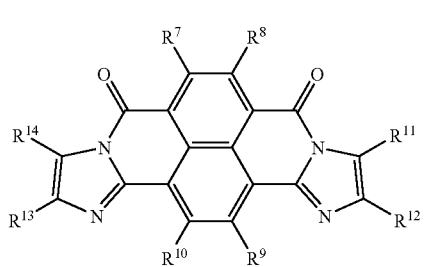

(IIb)

wherein $R^7$ to $R^{14}$, which may be the same or different, are a hydrogen atom, a halogen atom, a cyano group, an alkyl group, an aryl group, a fluoroalkyl group, an alkoxy group, an aryloxy group or a heterocyclic ring; and adjacent groups of $R^7$ to $R^{14}$ may be bonded to form an aromatic ring or a heterocyclic ring, and the aromatic ring or the heterocyclic ring may have a substituent.

3. A material for an organic electroluminescence device comprising a compound shown by the following formula (III):

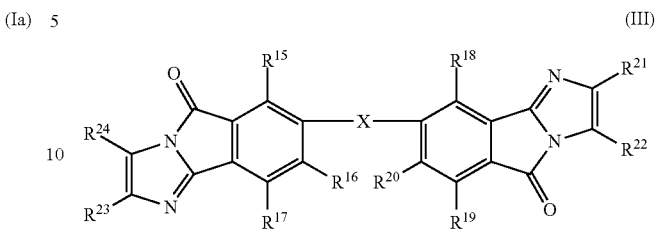

(III)

wherein $R^{15}$ to $R^{24}$, which may be the same or different, are a hydrogen atom, a halogen atom, a cyano group, an alkyl group, an aryl group, a fluoroalkyl group, an alkoxy group, an aryloxy group or a heterocyclic ring; adjacent groups of $R^{15}$ to $R^{24}$ may be bonded to form an aromatic ring or a heterocyclic ring, and the aromatic ring or the heterocyclic ring may have a substituent; and X is a single bond, —O—, —CO—, —S—, —SO—, —SO$_2$— or —CR$^{25}$R$^{26}$— wherein $R^{25}$ and $R^{26}$ are independently a hydrogen atom, a halogen atom, an alkyl group, an aryl group or a fluoroalkyl group, and $R^{25}$ and $R^{26}$ may be bonded to form a ring.

4. A material for an organic electroluminescence device comprising at least one of compounds shown by the following formula (IVa) or (IVb):

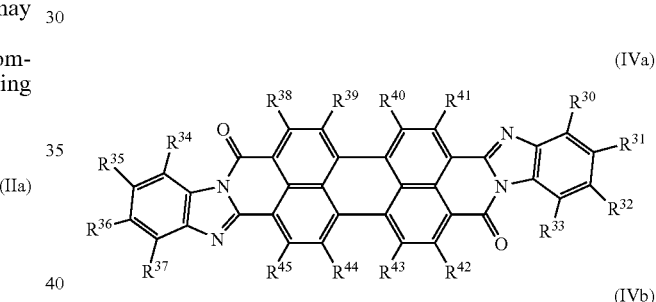

(IVa)

(IVb)

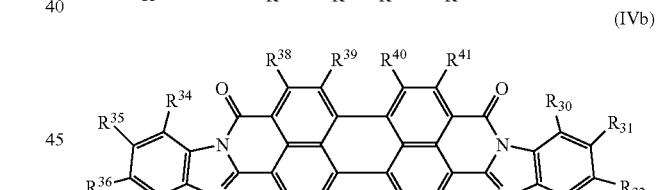

wherein $R^{30}$ to $R^{45}$, which may be the same or different, are a hydrogen atom, a halogen atom, a cyano group, an alkyl group, an aryl group, a fluoroalkyl group, an alkoxy group, an aryloxy group or a heterocyclic group; and adjacent groups of $R^{30}$ to $R^{37}$ may be bonded to form an aromatic ring or a heterocyclic ring, and the aromatic ring or the heterocyclic ring may have a substituent;

providing that the compound shown by the formula (IVa) or the compound shown by the formula (IVb) contains 6 or more fluorine atoms in its structure.

5. The material for an organic electroluminescence device according to any one of 1 to 4, which has a reduction potential in an acetonitrile solution of −1.0V (vsFc$^+$/Fc; where Fc means ferrocene) or more.

6. The material for an organic electroluminescence device according to any one of 1 to 5, which is a hole-injection material.

7. An organic electroluminescence device comprising an anode, a cathode and an organic thin film layer between the anode and the cathode, wherein
the organic thin film layer is a stack composed of a hole-injecting layer, a hole-transporting layer, an emitting layer and an electron-transporting layer being stacked sequentially from the anode, and
the hole-injecting layer comprises the material for an organic electroluminescence device according to any one of 1 to 6.

8. The organic electroluminescence device according to 7, wherein the hole-injecting layer further comprises a phenylenediamine compound shown by the following formula (V):

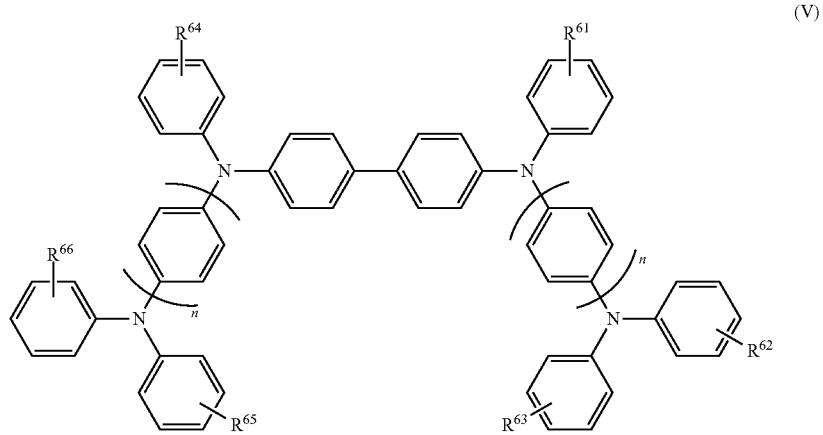

(V)

wherein $R^{61}$ to $R^{66}$, which may be the same or different, are a hydrogen atom, a halogen atom, a trifluoromethyl group, an alkyl group, an aryl group or a heterocyclic ring, or may form a naphthalene skeleton, a carbazole skeleton or a fluorene skeleton with a phenyl group bonding to $R^{61}$ to $R^{66}$; and n is 1 or 2.

9. A compound shown by the following formula (Ia), (Ib), (IIa), (IIb), (III), (IVa) or (IVb):

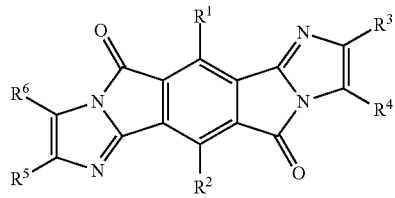

(Ia)

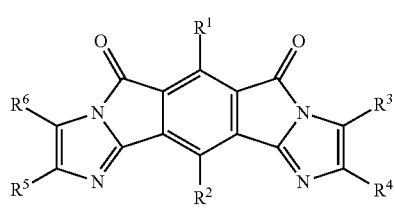

(Ib)

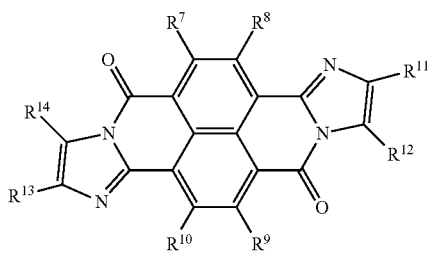

(IIa)

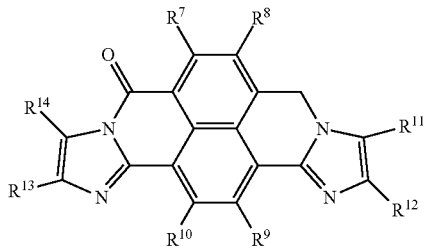

(IIb)

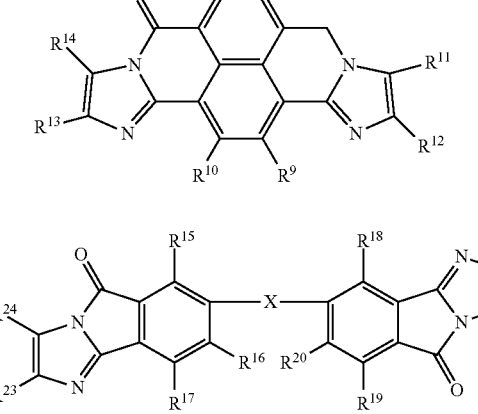

(III)

wherein $R^1$ to $R^{24}$, which may be the same or different, are a hydrogen atom, a halogen atom, a cyano group, an alkyl group, an aryl group, a fluoroalkyl group, an alkoxy group, an aryloxy group or a heterocyclic ring; and adjacent groups of $R^1$ to $R^{24}$ may be bonded to form an aromatic ring or a heterocylic ring, and the aromatic ring or the heterocyclic ring may have a substituent; and X is a single bond, —O—, —CO—, —S—, —SO—, —SO$_2$— or —CR$^{25}$R$^{26}$— wherein $R^{25}$ and $R^{26}$ are independently a hydrogen atom, a halogen atom, an alkyl group, an aryl group, or a fluoroalkyl group, and $R^{25}$ and $R^{26}$ may be bonded to form a ring;

providing that at least one of $R^7$ to $R^{14}$ in the formula (IIa) or (IIb) is a fluorine atom, a fluoroalkyl group or a cyano group;

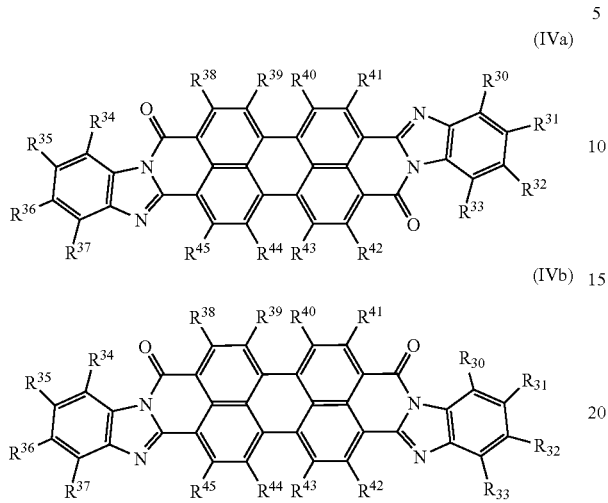

wherein $R^{30}$ to $R^{45}$, which may be the same or different, are a hydrogen atom, a halogen atom, a cyano group, an alkyl group, an aryl group, a fluoroalkyl group, an alkoxy group, an aryloxy group or a heterocyclic ring; adjacent groups of $R^{30}$ to $R^{37}$ may be bonded to form an aromatic ring or a heterocylic ring, and the aromatic ring or the heterocyclic ring may have a substituent;

providing that the compound shown by the formula (IVa) or the compound shown by the formula (IVb) contains 6 or more fluorine atoms in its structure.

According to the invention, a novel material for an organic EL device can be provided. Further, the invention can provide an organic EL device which can be driven at a lower voltage and has a prolonged device life.

BRIEF DESCRIPTION OF THE DRAWINGS

FIG. 1 is a schematic cross-sectional view showing one embodiment of the organic EL device of the invention.

BEST MODE FOR CARRYING OUT THE INVENTION

First, the material for an organic EL device of the invention will be explained.

The material for an organic EL device of the invention comprises at least one of compounds shown by the formula (Ia), (Ib), (IIa), (IIb), (III), (IVa) or (IVb):

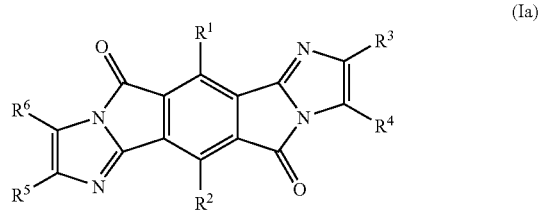

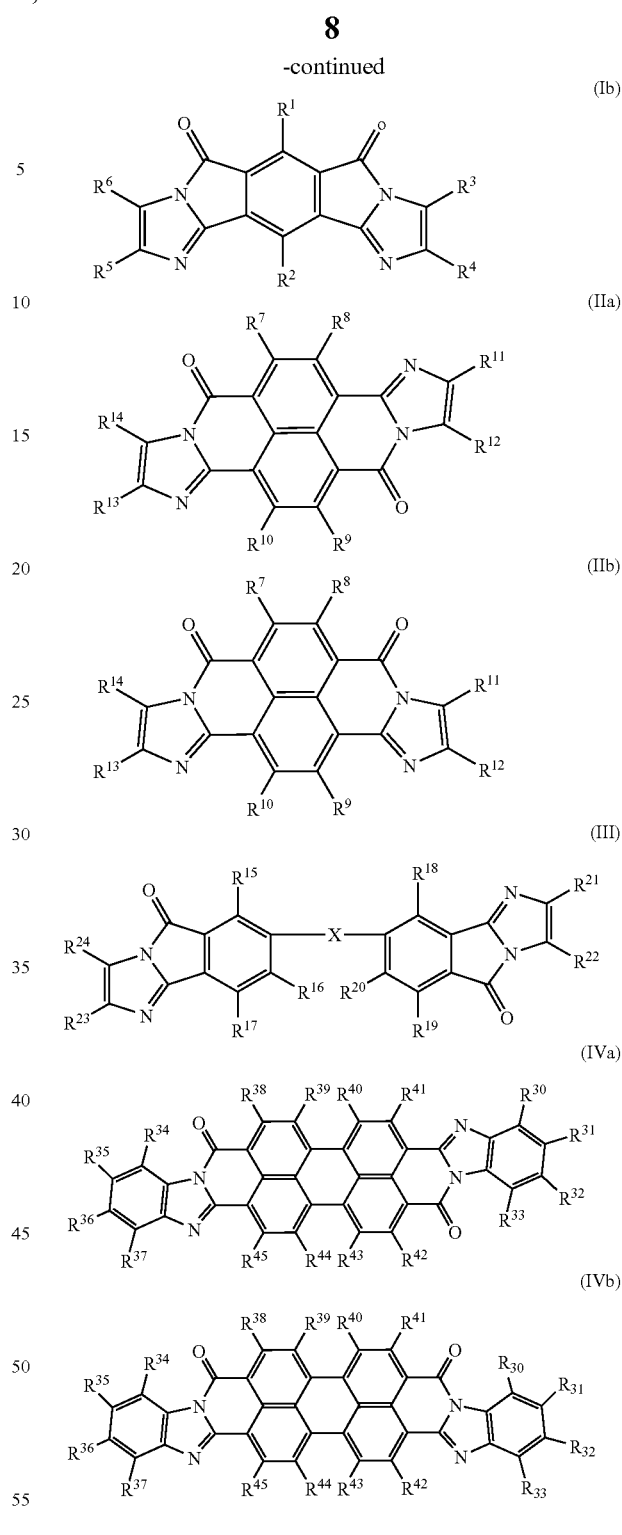

wherein $R^1$ to $R^{24}$, which may be the same or different, are a hydrogen atom, a halogen atom, a cyano group, an alkyl group, an aryl group, a fluoroalkyl group, an alkoxy group, an aryloxy group or a heterocyclic ring; adjacent groups of $R^1$ to $R^{24}$ may be bonded to form an aromatic ring or a heterocyclic ring, and the aromatic ring or the heterocyclic ring may have a substituent; X is a single bond, —O—, —CO—, —S—, —SO—, —SO$_2$— or —CR$^{25}$R$^{26}$—, wherein $R^{25}$ and $R^{26}$ are independently a hydrogen atom, a halogen atom, an alkyl group, an aryl group or a fluoroalkyl group and $R^{25}$ and $R^{26}$ may be bonded to form a ring; $R^{30}$ to $R^{45}$, which may be the same or different, are a hydrogen atom, a halogen atom, a cyano group, an alkyl group, an aryl group, a fluoroalkyl group, an alkoxy group, an aryloxy group or a heterocyclic ring; and adjacent groups of $R^{30}$ to $R^{37}$ may be bonded to form an aromatic ring or a heterocyclic ring, and the aromatic ring or the heterocyclic ring may have a substituent.

The compound shown by the formula (IVa) or the compound shown by the formula (IVb) contains 6 or more fluorine atoms in the structure thereof.

Examples of the halogen atom shown by $R^1$ to $R^{24}$, $R^{25}$, $R^{26}$ and $R^{30}$ to $R^{45}$ include a fluorine atom, a chlorine atom, a bromine atom and an iodine atom.

Examples of the alkyl group include methyl, ethyl, n-propyl, iso-propyl, n-butyl, iso-butyl, tert-butyl, cyclopentyl and cyclohexyl.

Examples of the aryl group include phenyl, biphenyl, naphthyl, fluorophenyl and trifluorophenyl.

Examples of the fluoroalkyl group include trifluoromethyl, pentafluoroethyl, perfluorocyclohexyl and perfluoroadamantyl.

Examples of the alkoxy group shown by $R^1$ to $R^{24}$ and $R^{30}$ to $R^{45}$ include methoxy, ethoxy and trifluoromethoxy.

Examples of the aryloxy group include benzyloxy, pentafluorobenzyloxy and 4-trifluoromethylbenzyloxy.

Examples of the heterocyclic ring include pyridine, pyrazine, furan, imidazole, benzimidazole and thiophene.

Each of the alkyl group, the aryl group, the fluoroalkyl group, the alkoxy group, the aryloxy group or the heterocyclic ring shown by $R^1$ to $R^{24}$ may be further substituted by a substituent. The substituent may be a halogen atom, a cyano group, an alkyl group, an aryl group, a fluoroalkyl group, an alkoxy group, an aryloxy group or a heterocyclic group as mentioned above. The same can be applied to the alkyl group, the aryl group and the fluoroalkyl group shown by $R^{25}$ and $R^{26}$.

Adjacent groups of $R^1$ to $R^{24}$ or $R^{25}$ and $R^{26}$ may be bonded each other to form an aromatic ring or a heterocyclic ring. Examples of the ring include a benzene ring, a naphthalene ring, a pyrazine ring, a pyridine ring and a furan ring. These rings may have a substituent. Examples of the substituent include a halogen atom, a cyano group, an alkyl group, an aryl group, a fluoroalkyl group, an alkoxy group, an aryloxy group or a heterocyclic ring.

For improving electron acceptability, keeping heat resistance and maintaining sublimation property, it is preferred that $R^1$ to $R^{24}$ contain a fluorine atom, a fluoroalkyl group or a cyano group. More preferably, at least one of $R^1$ to $R^6$ in the formula (Ia) or the formula (Ib) be a fluorine atom, a fluoroalkyl group or a cyano group, at least one of $R^7$ to $R^{14}$ in the formula (IIa) or the formula (IIb) is a fluorine atom, a fluoroalkyl group or a cyano group, and at least one of $R^{15}$ to $R^{24}$ in the formula (III) is a fluorine atom, a fluoroalkyl group or a cyano group.

The material for an organic EL device of the invention comprises at least one of compounds shown by the abovementioned formula (Ia), (Ib), (IIa), (IIb), (III), (IVa) or (IVb). They do not show only a particular isomer structure. For example, isomers shown by the formula (Ia) and by the formula (Ib) are produced depending on the synthesis method. The material of the invention is not limited to a particular isomer. The material of the invention may be a compound with a single structure or may be a mixture of isomers.

If it is a mixture, it is preferred that it may be a mixture of a compound shown by the formula (Ia) and a compound shown by the formula (Ib), a mixture of a compound shown by the formula (IIa) and a compound shown by the formula (IIb) or a mixture of a compound shown by the formula (IVa) and a compound shown by the formula (IVb).

Due to the structure shown by each of the above formulas, in the material for an organic EL device of the invention, stability such as heat resistance or sublimation property, or the electron acceptability of the compound can be enhanced. These compounds have electron acceptability, are improved in heat resistance. Since they are capable of being purified by sublimation, they can be highly purified. Furthermore, when used in an organic EL device, the driving voltage of the organic EL device can be lowered. In addition, the device life can also be prolonged. Since these compounds do not scatter inside of a film-forming apparatus during the production of a device, they are free from the fear that a film-forming apparatus or an organic EL device is contaminated.

Therefore, these compounds are preferable as a material for an organic EL device, in particular, as a hole-injecting material.

It is preferred that the material for an organic EL device of the invention have a reduction potential in an acetonitrile solution of $-1.0V(vsFc^+/Fc)$ or more, with $-0.8V(vsFc^+/Fc)$ or more being particularly preferable. Here, Fc means ferrocene. By using a compound with a reduction potential of $-1.0V$ or more, electron acceptability can be more improved.

Due to increased electron acceptability, electron transfer with an anode made of ITO or a material having a work function lower than that of ITO can be easily conducted. Further, holes can be injected more easily since the HOMO level of a hole-transporting material and the LUMO level of an electron-accepting compound become closer.

Specific examples of the material for an organic EL device of the invention will be given below.

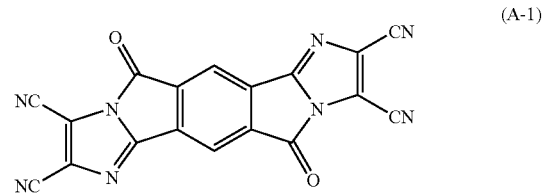

(A-1)

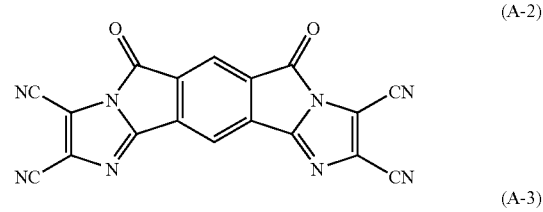

(A-2)

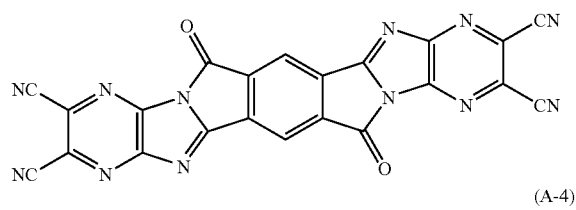

(A-3)

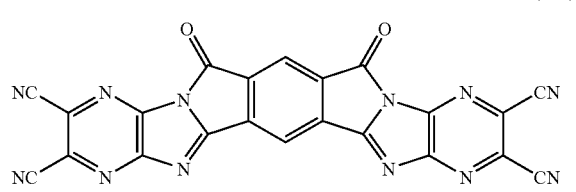

(A-4)

(A-5)
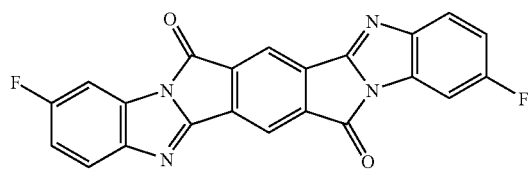
(A-6)
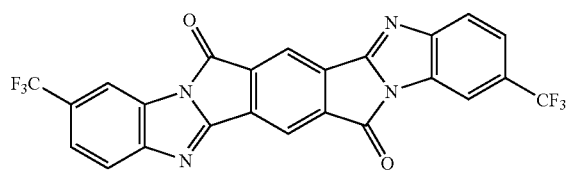
(A-7)
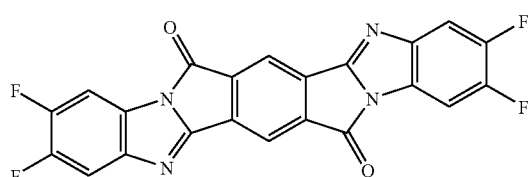
(A-8)
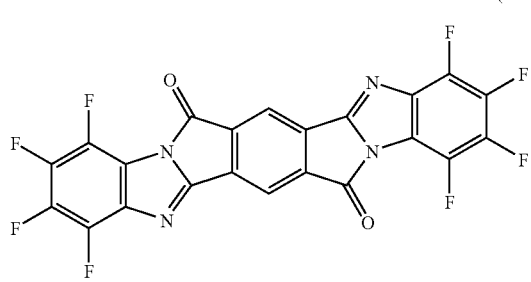
(A-9)
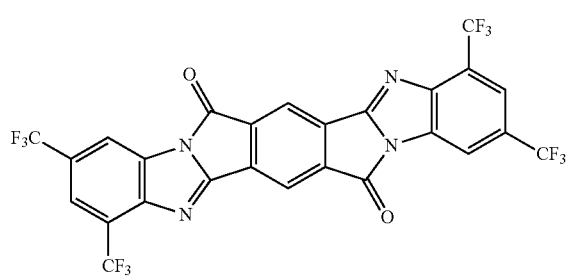
(A-10)
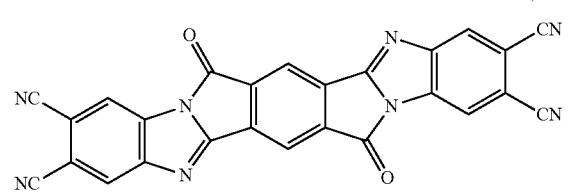
(A-11)
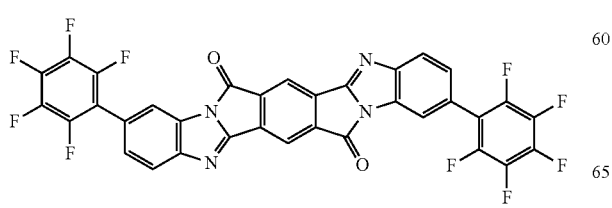
(A-12)
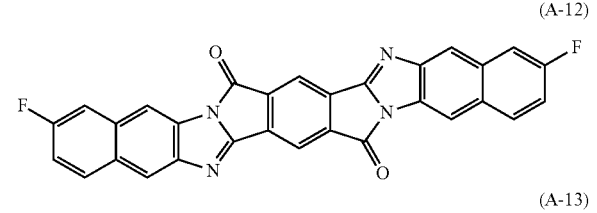
(A-13)
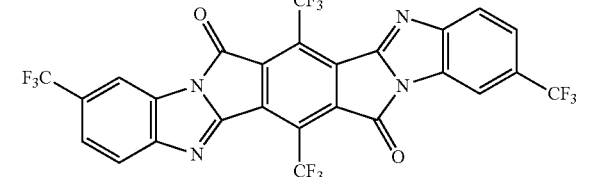
(A-14)
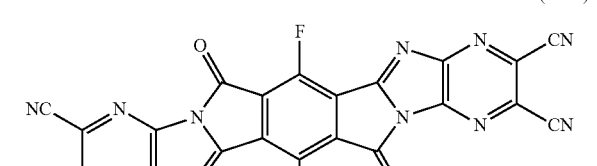
(A-15)
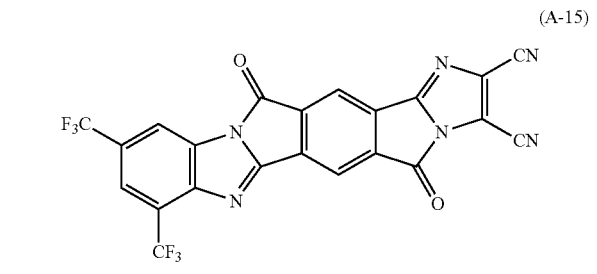
(A-16)
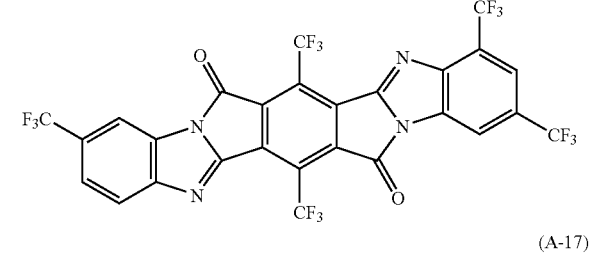
(A-17)
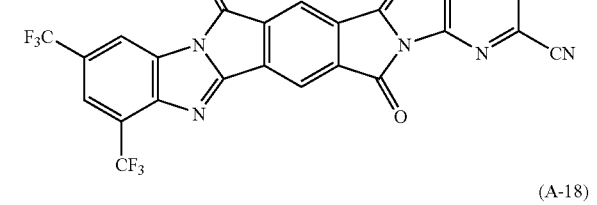
(A-18)
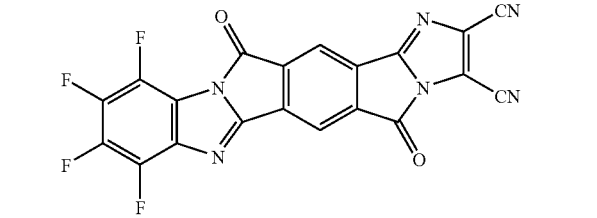

-continued
(B-1)
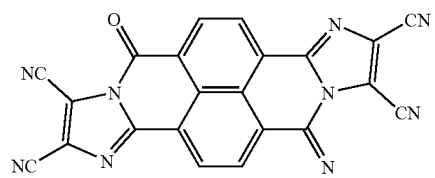
(B-2)
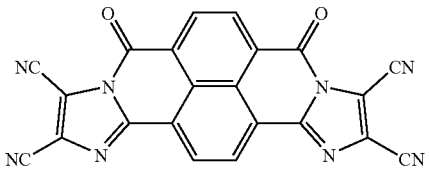
(B-3)
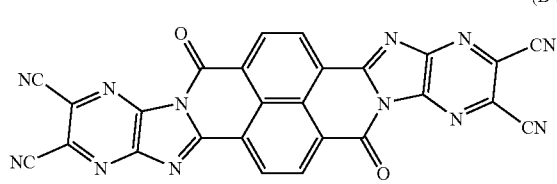
(B-4)
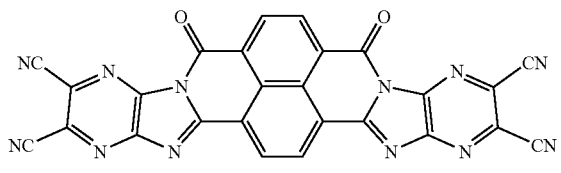
(B-5)
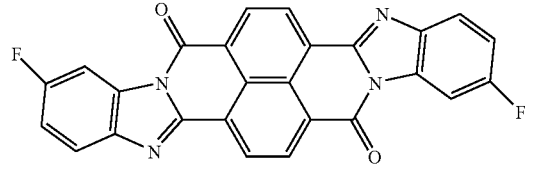
(B-6)
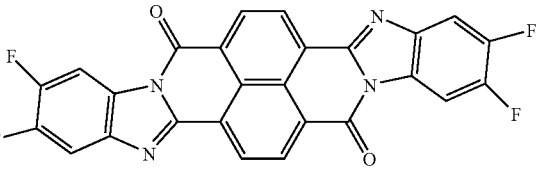
(B-7)
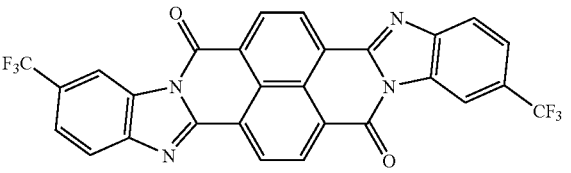
(B-8)
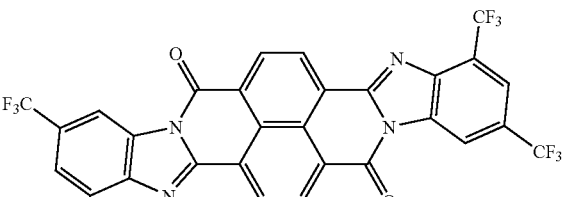
-continued
(B-9)
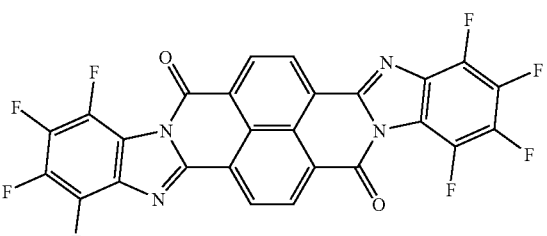
(B-10)
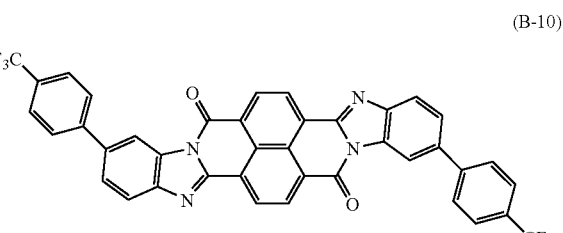
(B-11)
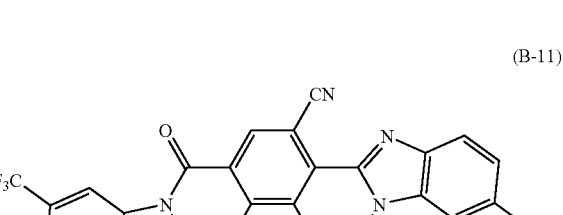
(B-12)
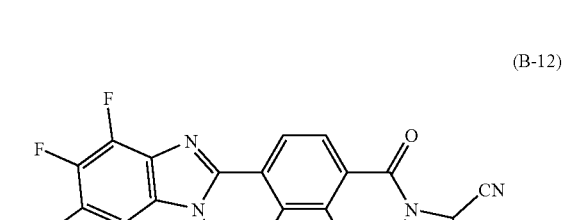
(B-13)
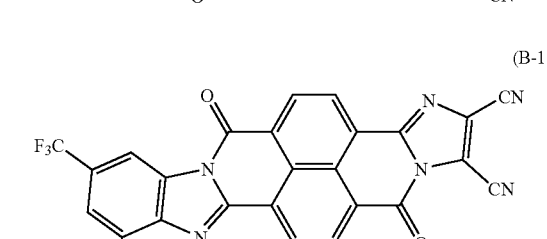
(B-14)
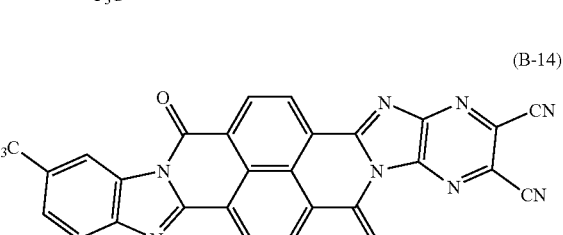

-continued
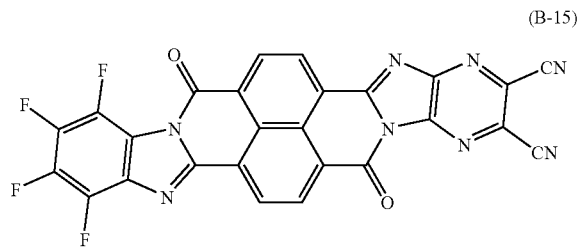
(B-15)
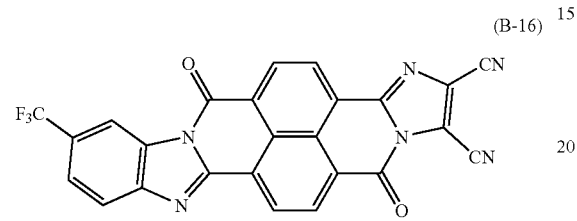
(B-16)
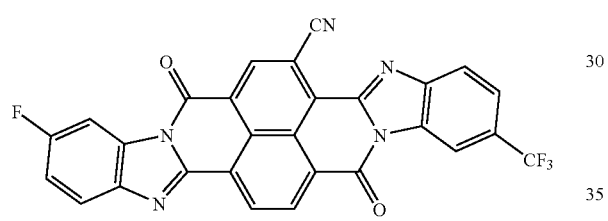
(B-17)
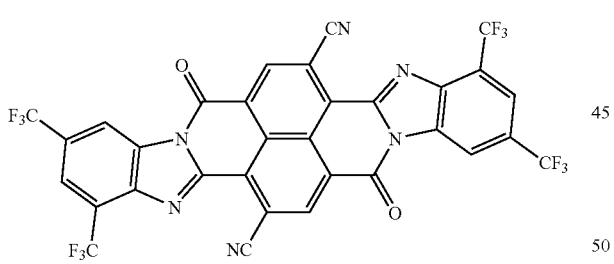
(B-18)
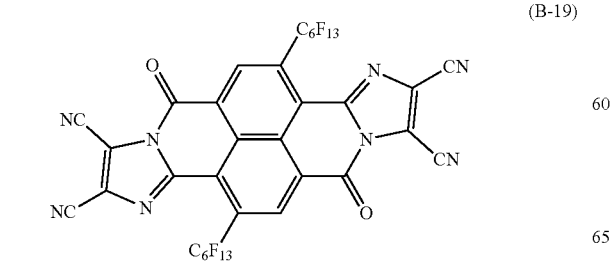
(B-19)
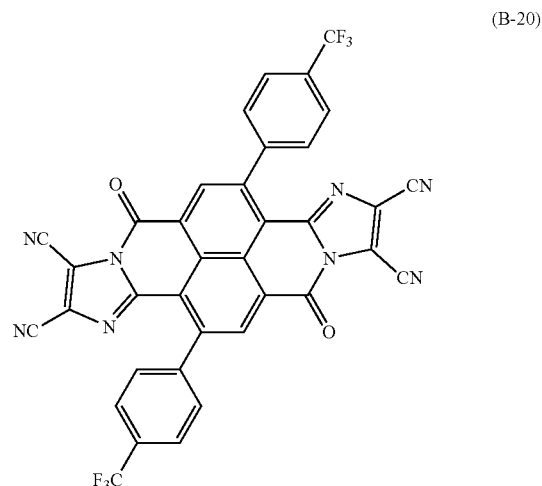
(B-20)
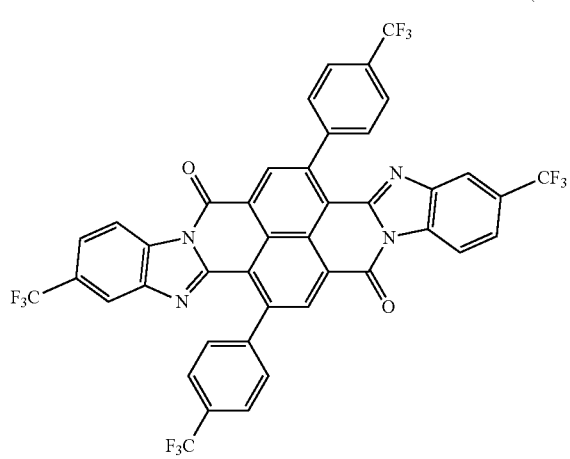
(B-21)
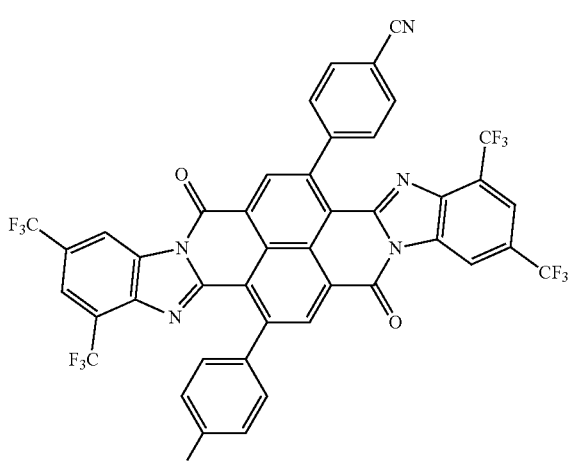
(B-22)
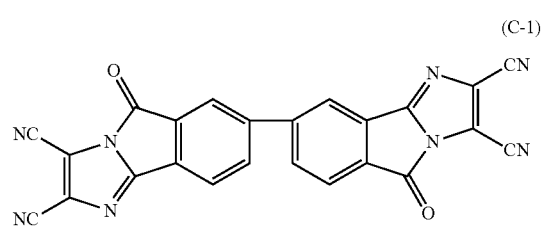
(C-1)

(C-2) 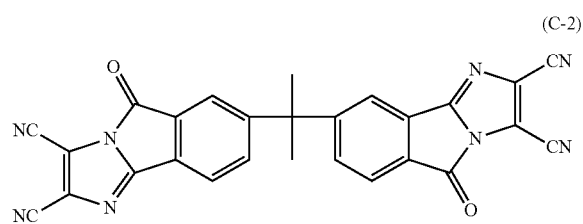
(C-3) 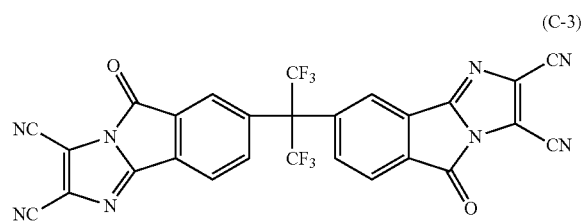
(C-4) 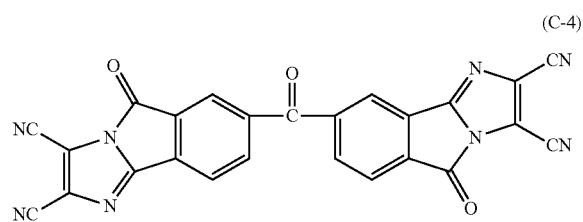
(C-5) 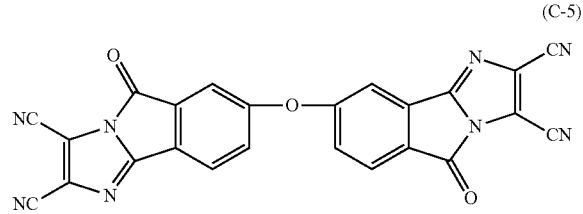
(C-6) 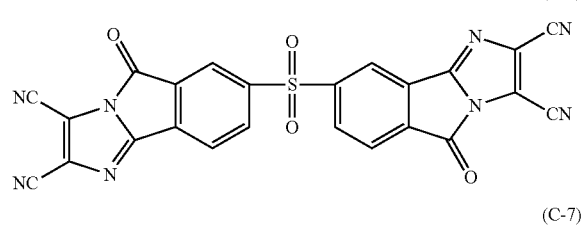
(C-7) 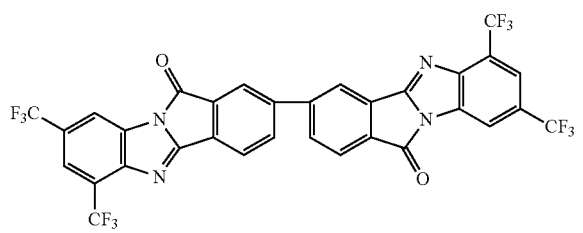
(C-8) 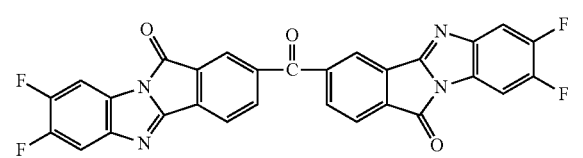
(C-9) 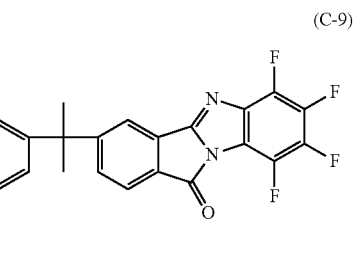
(C-10) 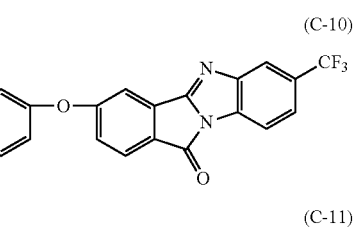
(C-11) 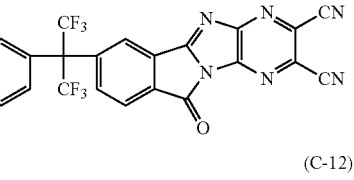
(C-12) 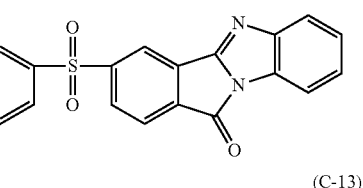
(C-13) 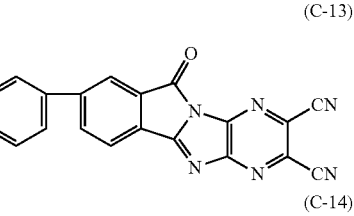
(C-14) 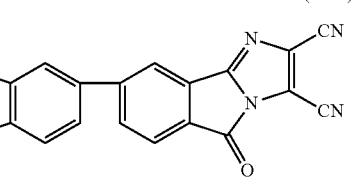
(C-15) 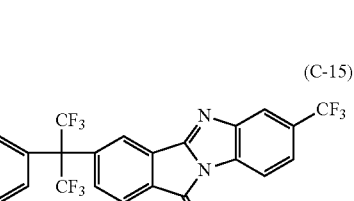
(C-16) 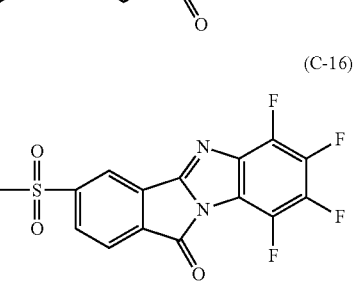

(P-1)
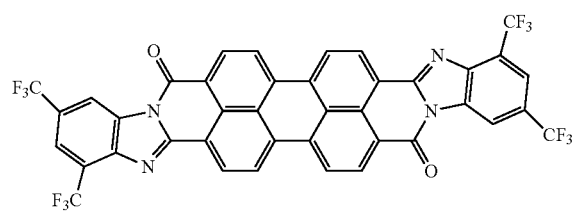
(P-2)
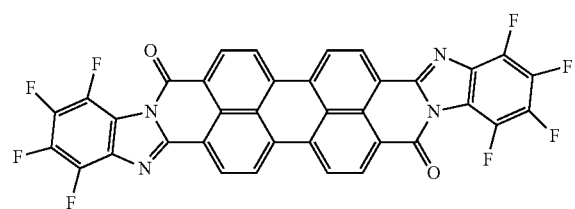
(P-3)
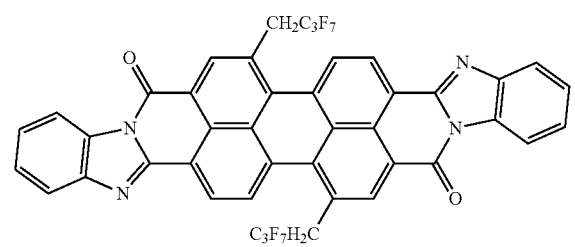
(P-4)
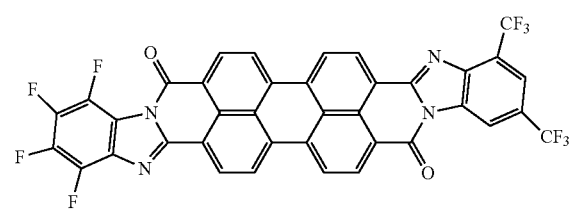
(P-5)
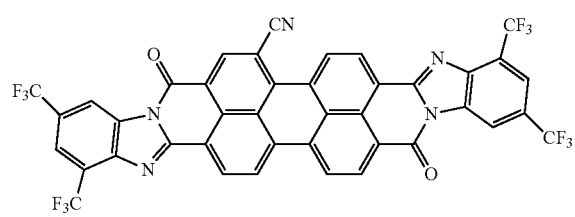
(P-6)
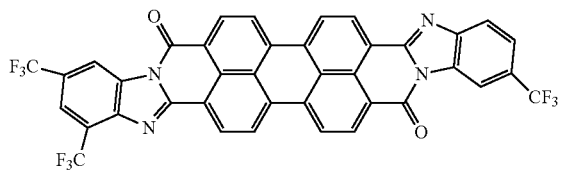
The compound of the invention can be synthesized by a method shown by the following synthesis schemes 1 to 4, for example.
(Synthesis scheme 1)
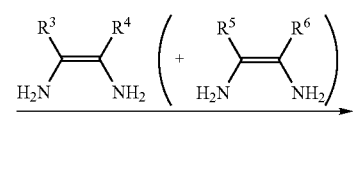
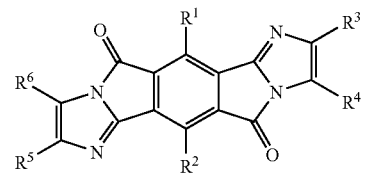
(Synthesis scheme 2)
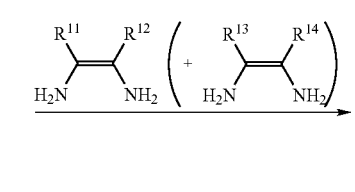
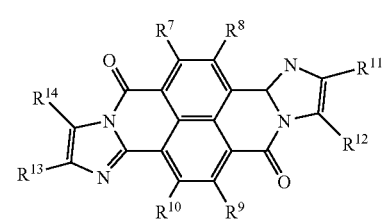

(Synthesis scheme 3)

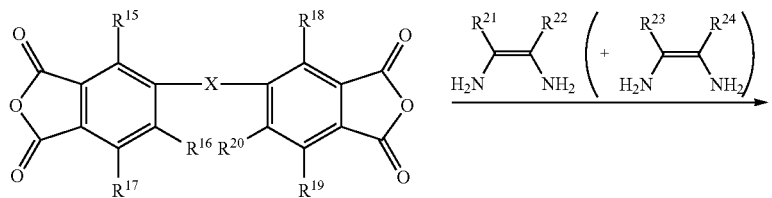

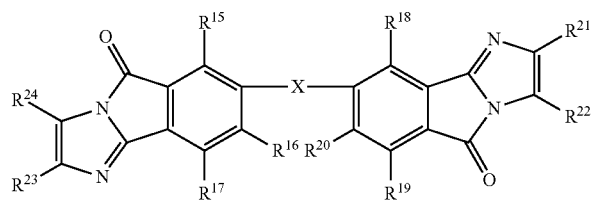

(In the formula, $R^1$ to $R^{24}$ and X are the same as those in the above-mentioned formulas (I) to (III))

(Synthesis scheme 4)

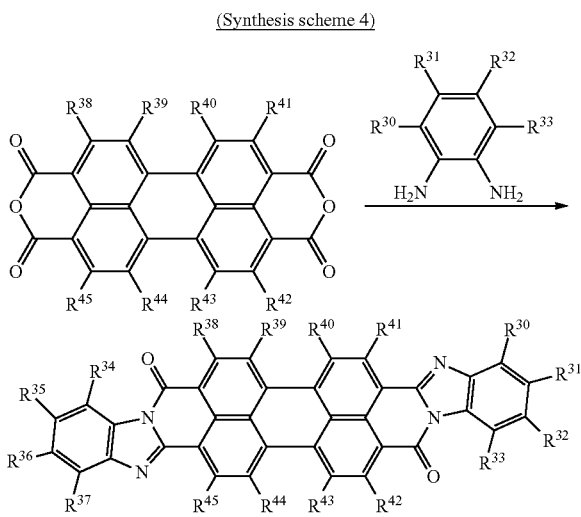

(In the formula, $R^{30}$ to $R^{45}$ are the same as those in the above-mentioned formulas (IVa) and (IVb))

The compound of the invention can be synthesized by heating tetracarboxylic anhydride and a diamine compound as raw materials in a solvent such as acetic acid, pyridine, dimethylformamide, dimethylacetoamide, toluene, xylene or ethanol to 50 to 220° C. If need arises, a catalyst such as zinc acetate may be used. In this reaction, it is possible to allow two types of diamine compounds to react simultaneously or to allow one diamine compound to react first, followed by reaction of the other diamine compound. A reaction product may be subjected to purification or isomer separation by column chromatography by using silica gel, alumina or the like. Further, it can be highly purified by purification by sublimation.

Next, an explanation is made on the organic EL device of the invention.

The organic EL device of the invention has an organic thin film layer between an anode and a cathode. The organic thin film layer comprises a hole-injecting layer, a hole-transporting layer, an emitting layer and an electron-transporting layer in sequential order, and the hole-injecting layer contains the material for an organic EL device of the invention.

FIG. 1 is a schematic cross-sectional view showing one embodiment of the organic EL device of the invention.

In an organic EL device 1, on a substrate (not shown), an anode 10, a hole-injecting layer 20, a hole-transporting layer 30, an emitting layer 40, an electron-transporting layer 50 and a cathode 60 are stacked in sequential order. In this device, the organic thin film layer is of a stacked structure comprising the hole-injecting layer 20, the hole-transporting layer 30, the emitting layer 40 and the electron-transporting layer 50. In the invention, the hole-injecting layer 20 contains the material for an organic EL device of the invention. As a result, lowering in driving voltage of an organic EL device and prolongation of a device life can be attained.

In the meantime, other organic layers than the hole-injecting layer may contain the material for an organic EL device of the invention. In this case, the material for an organic EL device can be used in a mixture with a material constituting each layer mentioned later.

The material for an organic EL device of the invention in the hole-injecting layer is preferably 1 to 100 mol %.

It is preferred that the organic EL device of the invention contain, in addition to at least one of compounds shown by the above-mentioned formulas (Ia), (Ib), (IIa), (IIb), (III), (IVa) or (IVb), a phenylenediamine compound shown by the following formula (V):

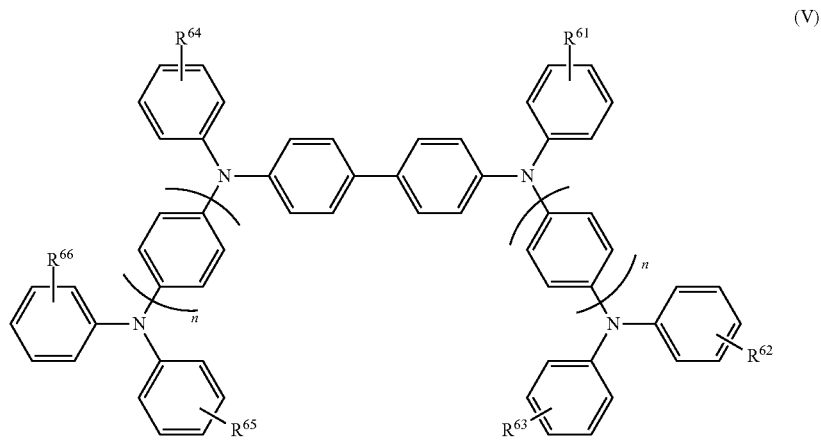

(V)

In the formula, $R^{61}$ to $R^{66}$, which may be the same or different, are a hydrogen atom, a halogen atom, a trifluoromethyl group, an alkyl group, an aryl group or a heterocyclic ring, and may form a naphthalene skeleton, a carbazole skeleton or a fluorene skeleton with a phenyl group bonding to $R^{61}$ to $R^{66}$; and n is 1 or 2.

When this phenylenediamine compound is contained, as compared with the case where the compound of the invention is used alone, the film uniformity, heat resistance or electron injection property may be improved.

As the halogen atom shown by $R^{61}$ to $R^{66}$, a fluorine atom is preferable.

As the alkyl group shown by $R^{61}$ to $R^{66}$, a methyl group, an isopropyl group, a tert-butyl group and a cyclohexy group are preferable, for example.

As the aryl group shown by $R^{61}$ to $R^{66}$, a phenyl group, a naphthyl group and a fluorenyl group are preferable. They may be substituted by a methyl group or the like.

As the heterocycle shown by $R^{61}$ to $R^{66}$, a pyridine ring and a pyrazine ring are preferable, for example.

$R^{61}$ to $R^{66}$ may form a naphthalene skeleton, a carbazole skeleton or a fluorene skeleton with a phenyl group bonding to $R^{61}$ to $R^{66}$. They may be substituted by a methyl group or the like.

The content of the compound shown by the formula (IV) in the hole-injecting layer is preferably 0.1 to 98 mol %.

The mixing ratio of the compound shown by the above-mentioned formula (Ia), (IIa), (IIb), (III), (IVa) or (IVb) and the phenylenediamine compound shown by the formula (V) may be appropriately selected according to the material for an anode.

Preferred examples of the compound shown by the formula (V) are given below.

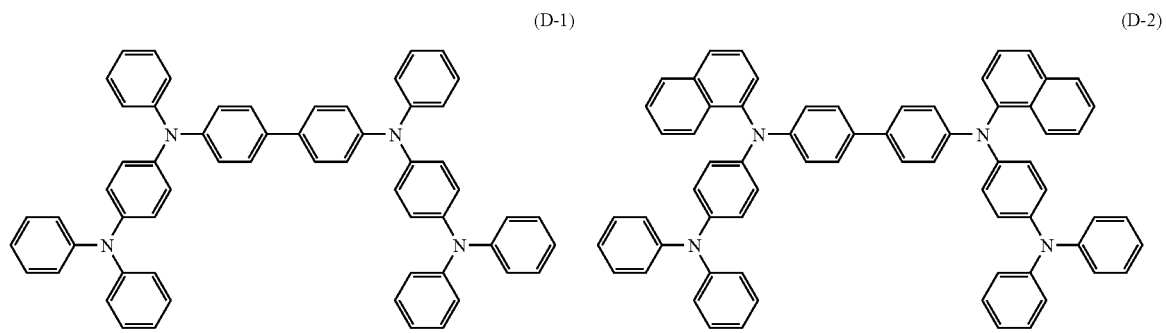

(D-1)　　　　(D-2)

-continued
(D-3)
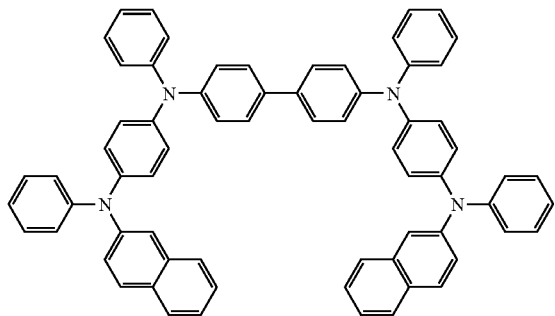
(D-4)
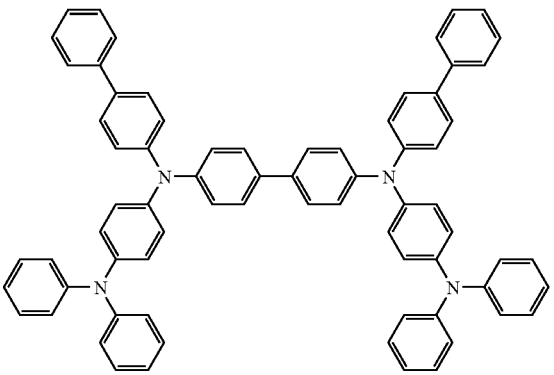
(D-5)
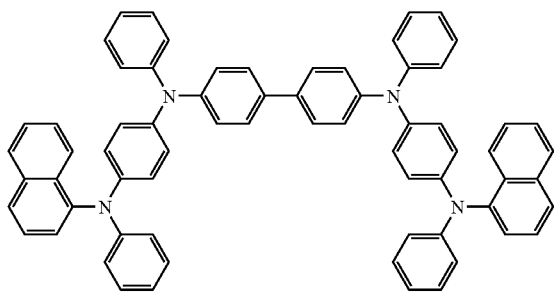
(D-6)
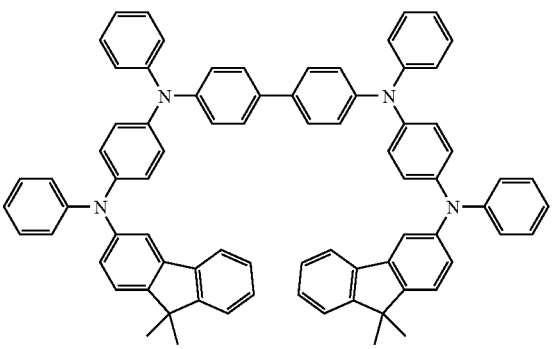
(D-7)
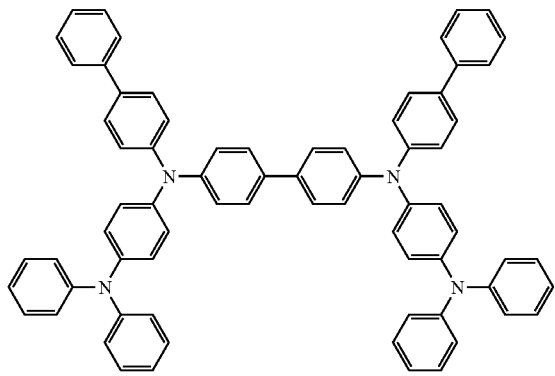
(D-8)
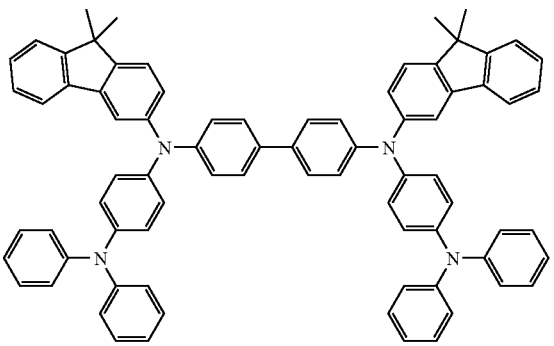
(D-9)
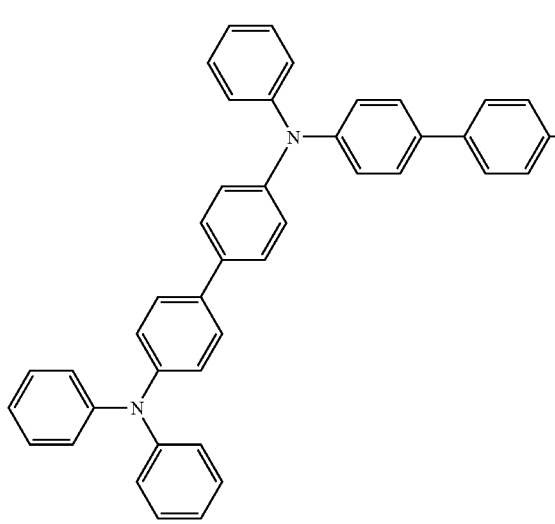
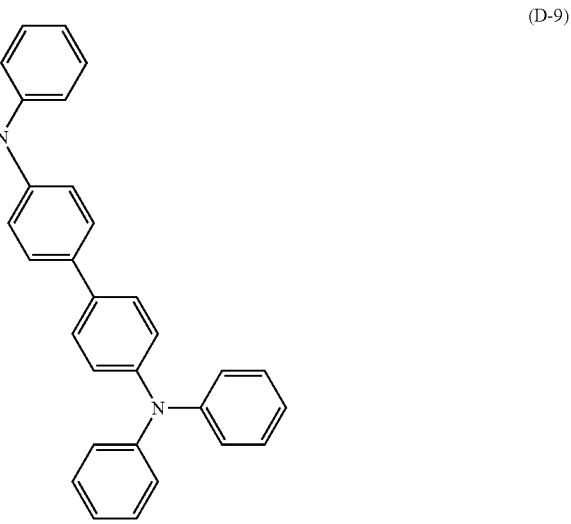

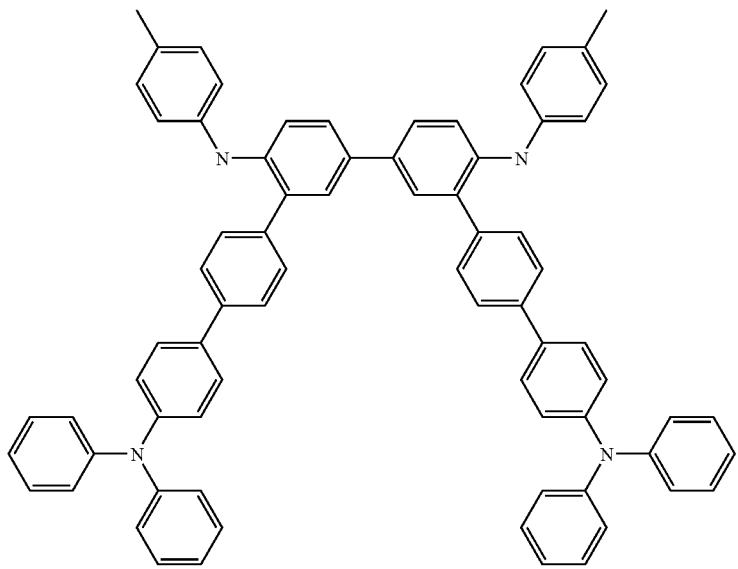
(D-10)
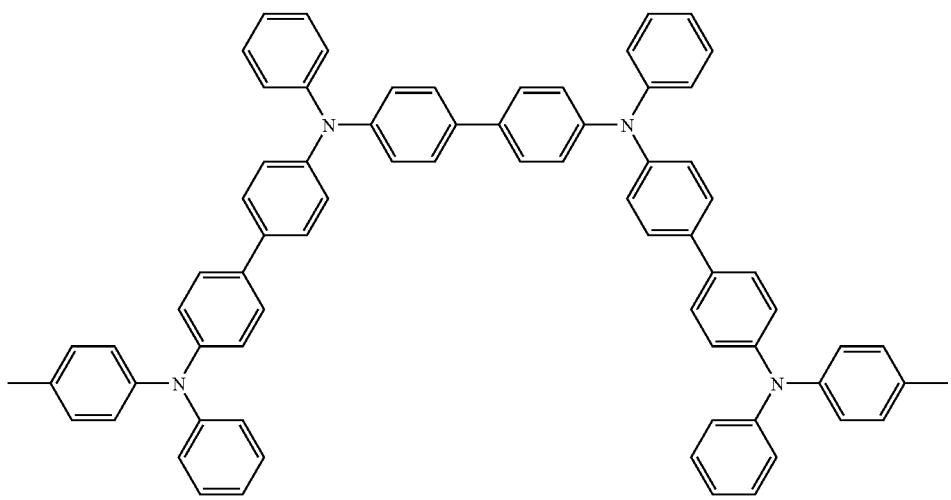
(D-11)
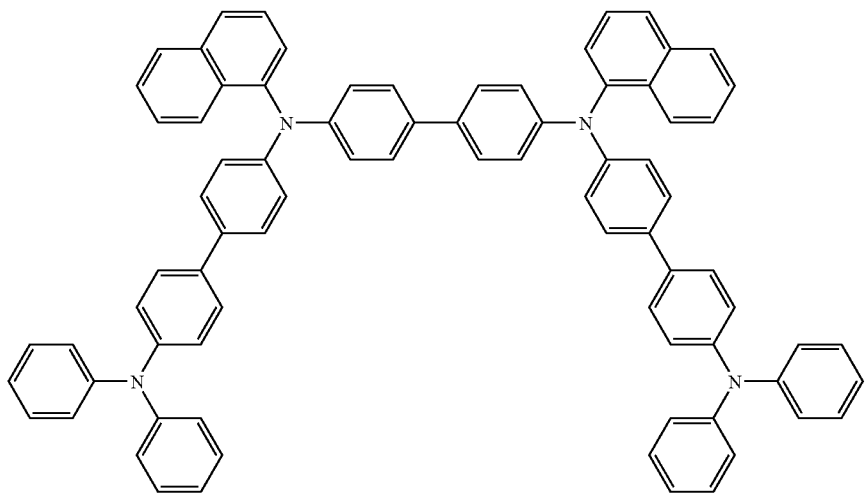
(D-12)

The material for an organic EL device of the invention can be used in a device with a configuration other than the configuration in the above-mentioned embodiment. For example, it may be used in a device with the following configurations (1) to (15) as a material for each of the organic layers constituting the device, such as an emitting layer.
(1) Anode/emitting layer/cathode
(2) Anode/hole-transporting layer/emitting layer/cathode
(3) Anode/emitting layer/electron-transporting layer/cathode
(4) Anode/hole-transporting layer/emitting layer/electron-transporting layer/cathode
(5) Anode/hole-transporting layer/emitting layer/adhesion-improving layer/cathode
(6) Anode/hole-injecting layer/hole-transporting layer/emitting layer/electron-transporting layer/cathode (FIG. 1)
(7) Anode/hole-transporting layer/emitting layer/electron-transporting layer/electron-injecting layer/cathode
(8) Anode/hole-injecting layer/hole-transporting layer/emitting layer/electron-transporting layer/electron-injecting layer/cathode
(9) Anode/insulating layer/hole-transporting layer/emitting layer/electron-transporting layer/cathode
(10) Anode/hole-transporting layer/emitting layer/electron-transporting layer/insulating layer/cathode
(11) Anode/inorganic semiconductor layer/insulating layer/hole-transporting layer/emitting layer/insulating layer/cathode
(12) Anode/insulating layer/hole-transporting layer/emitting layer/electron-transporting layer/insulating layer/cathode
(13) Anode/hole-injecting layer/hole-transporting layer/emitting layer/electron-transporting layer/insulating layer/cathode
(14) Anode/insulating layer/hole-injecting layer/hole-transporting layer/emitting layer/electron-transporting layer/electron-injecting layer/cathode
(15) Anode/insulating layer/hole-injecting layer/hole-transporting layer/emitting layer/electron-transporting layer/electron-injecting layer/insulating layer/cathode Among these, usually, the configurations (4), (6), (7), (8), (12), (13) and (15) are preferably used.

Each member constituting the organic EL device of the invention will be described below.

(Transparent Substrate)

The organic EL device is usually formed on a transparent substrate. The transparent substrate is a substrate for supporting the organic EL device, and is preferably a flat and smooth substrate having a 400-to-700-nm-visible-light transmittance of 50% or more.

Specific examples thereof include glass plates and polymer plates. Examples of the glass plate include soda-lime glass, barium/strontium-containing glass, lead glass, aluminosilicate glass, borosilicate glass, barium borosilicate glass, and quartz. Examples of the polymer plate include polycarbonate, acrylic polymer, polyethylene terephthalate, polyethersulfide, and polysulfone.

Transparency is not required when the supporting substrate is positioned in the direction opposite to the light-outcoupling direction.

(Anode)

The anode of the organic EL device plays a role for injecting holes into its hole-transporting layer or emitting layer. When transparency is required for the anode, indium tin oxide alloy (ITO), tin oxide (NESA), indium zinc oxide alloy (IZO), gold, silver, platinum, copper, and the like may be used as the material for the anode. When a reflective electrode which does not require transparency is used, a metal such as aluminum, molybdenum, chromium, and nickel or alloys thereof may also be used.

In particular, when an anode having a low work function (5.0 eV or less, for example) is used in combination with a hole-injecting layer using the material for an organic EL device of the invention, electron transfer is possible and the anode exhibits good injection properties.

Although these materials may be used individually, alloys thereof or materials wherein another element is added to the materials can be appropriately selected for use.

The anode can be formed by forming these electrode materials into a thin film by a method such as vapor deposition and sputtering.

In the case where emission from the emitting layer is outcoupled through the anode, the transmittance of the anode to the emission is preferably more than 10%. The sheet resistance of the anode is preferably several hundred $\Omega/\square$ or less. The film thickness of the anode, which varies depending upon the material thereof, is usually from 1 nm to 1 μm, preferably from 10 to 200 nm.

In particular, when an anode having a low work function (5.0 eV or less, for example) is used in combination with a hole-injecting layer using the material for an organic EL device of the invention, electron transfer is possible and the anode exhibits good injection properties.

(Emitting Layer)

The emitting layer of the organic EL device has the following functions (1), (2) and (3) in combination.

(1) Injection function: function of allowing injection of holes from the anode or hole-injecting layer and injection of electrons from the cathode or electron-injecting layer upon application of an electric field
(2) Transporting function: function of moving injected carriers (electrons and holes) due to the force of an electric field
(3) Emitting function: function of allowing electrons and holes to recombine to emit light Note that electrons and holes may be injected into the emitting layer with different degrees, or the transportation capabilities indicated by the mobility of holes and electrons may differ. It is preferable that the emitting layer move either electrons or holes.

As the method of forming the emitting layer, a known method such as deposition, spin coating, or an LB method may be applied. It is preferable that the emitting layer be a molecular deposition film. The molecular deposition film is a thin film formed by deposition of a material compound in a vapor phase condition or a film formed by solidification of a material compound in a solution or liquid phase condition, and is distinguished from a thin film (molecular accumulation film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by spin coating or the like, as disclosed in JP-A-57-51781.

In the invention, if need arises, known emitting materials other than the emitting materials formed of the novel compound of the invention may be contained in the emitting layer insofar as the object of the invention is not impaired. An emitting layer containing other known emitting materials may be stacked on the emitting layer containing the emitting materials formed of the novel compound of the invention.

As the emitting material or the doping material used for the emitting layer, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, a quinoline metal complex, an aminoquinoline metal complex, a benzoquinoline metal complex, imine, diphenyl ethylene, vinylanthracene, diaminocarbazole, pyran, thiopyran, polymethine, merocyanine, an imidazole chelate oxanoid compound, quinacridone, rubrene, a fluorescent pigment and like can be given. Note that the emitting material and the doping material are not limited to these compounds.

As the host material for use in the emitting layer, the compounds represented by the following formulas (i) to (ix) are preferred.

Asymmetrical anthracene represented by the following formula (i):

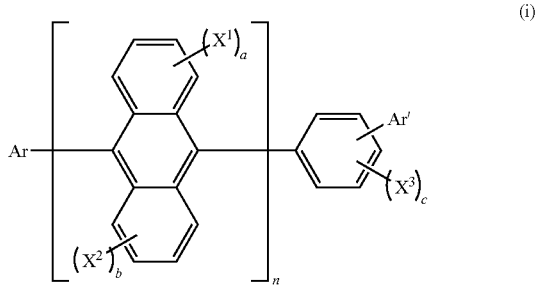

(i)

wherein Ar is a substituted or unsubstituted fused aromatic group having 10 to 50 carbon atoms that form a ring (hereinafter referred to as a "ring carbon atom"), Ar' is a substituted or unsubstituted aromatic group having 6 to 50 ring carbon atoms, $X^1$ to $X^3$ are independently a substituted or unsubstituted aromatic group having 6 to 50 ring carbon atoms, a substituted or unsubstituted aromatic heterocyclic group having 5 to 50 atoms that form a ring (hereinafter referred to as a "ring atom"), a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group or a hydroxyl group, a, b and c are each an integer of 0 to 4, n is an integer of 1 to 3, and when n is two or more, the groups in [ ] may be the same or different.

Asymmetrical monoanthracene derivatives represented by the following formula (ii):

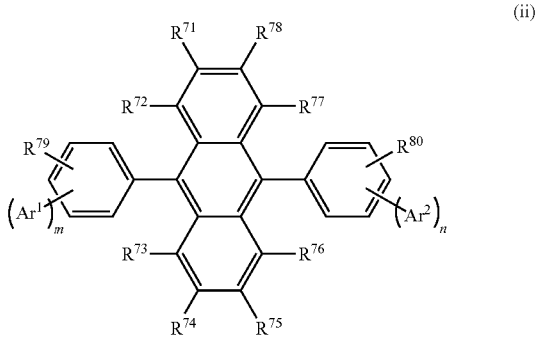

(ii)

wherein $Ar^1$ and $Ar^2$ are independently a substituted or unsubstituted aromatic ring group having 6 to 50 ring carbon atoms, and m and n are each an integer of 1 to 4, provided that in the case where m=n=1 and $Ar^1$ and $Ar^2$ are symmetrically bonded to the benzene rings, $Ar^1$ and $Ar^2$ are not the same, and in the case where m or n is an integer of 2 to 4, m is different from n; and $R^{71}$ to $R^{80}$ are independently a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group.

Asymmetrical pyrene derivatives represented by the following formula (iii):

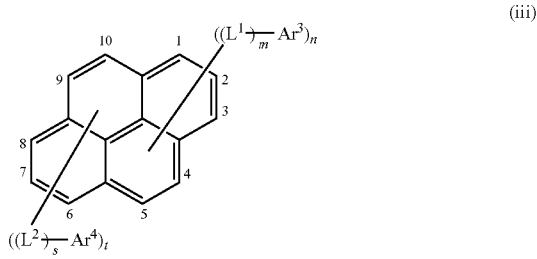

(iii)

wherein $Ar^3$ and $Ar^4$ are independently a substituted or unsubstituted aromatic group having 6 to 50 ring carbon atoms;

$L^1$ and $L^2$ are each a substituted or unsubstituted phenylene group, a substituted or unsubstituted naphthalenylene group, a substituted or unsubstituted fluorenylene group, or a substituted or unsubstituted dibenzosilolylene group;

m is an integer of 0 to 2, n is an integer of 1 to 4, s is an integer of 0 to 2, and t is an integer of 0 to 4; and $L^1$ or $Ar^3$ bonds at any one position of 1 to 5 of the pyrene, and $L^2$ or $Ar^4$ bonds at any one position of 6 to 10 of the pyrene;

provided that when n+t is an even number, $Ar^3$, $Ar^4$, $L^1$ and $L^2$ satisfy the following (1) or (2):

(1) $Ar^3 \neq Ar^4$ and/or $L^1 \neq L^2$ where ≠ means these substituents are groups having different structures from each other.

(2) when $Ar^3 = Ar^4$ and $L^1 = L^2$, (2-1) m≠s and/or n≠t, or (2-2) when m=s and n=t, (2-2-1) $L^1$ and $L^2$, or the pyrene each bond to $Ar^3$ and $Ar^4$ at different positions, or (2-2-2)

When $L^1$ and $L^2$, or the pyrene each bond to $Ar^3$ and $Ar^4$ at the same positions, the pyrene is neither substituted by $L^1$ and $L^2$, or $Ar^3$ and $Ar^4$ at 1 and 6 positions, nor 2 and 7 positions.

Asymmetrical anthracene represented by the following formula (iv):

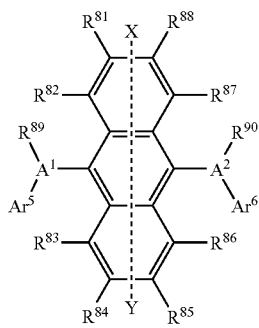

(iv)

wherein $A^1$ and $A^2$ are independently a substituted or unsubstituted fused aromatic ring group having 10 to 20 ring carbon atoms, $Ar^5$ and $Ar^6$ are independently a hydrogen atom or a substituted or unsubstituted aromatic ring group with 6 to 50 ring carbon atoms, $R^{81}$ to $R^{90}$ are independently a hydrogen atom or a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group, and each of $Ar^5$, $Ar^6$, $R^{89}$ and $R^{90}$ may be plural, and adjacent groups thereof may form a saturated or unsaturated ring structure, provided that groups do not symmetrically bond to 9 and 10 positions of the central anthracene with respect to X-Y axis in the formula (iv).

Anthracene derivatives represented by the following formula (v):

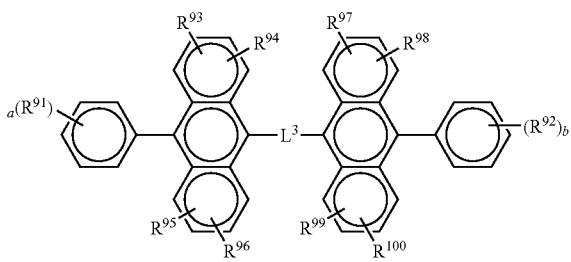

(v)

wherein $R^{91}$ to $R^{100}$ are independently a hydrogen atom, an alkyl group, a cycloalkyl group, an aryl group which may be substituted, an alkoxy group, an aryloxy group, an alkylamino group, an alkenyl group, an arylamino group or a heterocyclic group which may be substituted; a and b are each an integer of 1 to 5; when they are 2 or more, $R^{91}$s or $R^{92}$s may be the same or different, or $R^{91}$s or $R^{92}$s may be bonded together to form a ring; $R^{93}$ and $R^{94}$, $R^{95}$ and $R^{96}$, $R^{97}$ and $R^{98}$, or $R^{99}$ and $R^{100}$ may be bonded together to form a ring; and $L^3$ is a single bond, —O—, —S—, —N(R)— (R is an alkyl group or a substituted or unsubstituted aryl group), an alkylene group or an arylene group.

Anthracene derivatives represented by the following formula (vi):

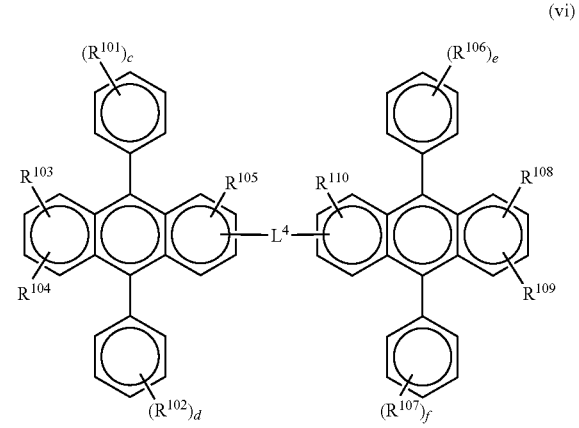

(vi)

wherein $R^{101}$ to $R^{110}$ are independently a hydrogen atom, an alkyl group, a cycloalkyl group, an aryl group, an alkoxy group, an aryloxy group, an alkylamino group, an arylamino group or a heterocyclic group which may be substituted; c, d, e and f are each an integer of 1 to 5; when they are 2 or more, $R^{101}$s, $R^{102}$s, $R^{106}$s, or $R^{107}$s may be the same or different, $R^{101}$s, $R^{102}$s, $R^{106}$s or $R^{107}$s may be bonded to each other to form a ring, or $R^{103}$ and $R^{104}$, or $R^{108}$ and $R^{109}$ may be bonded to each other to form a ring; and $L^4$ is a single bond, —O—, —S—, —N(R)— (R is an alkyl group or a substituted or unsubstituted aryl group), an alkylene group or an arylene group.

Spirofluorene derivatives represented by the following formula (vii):

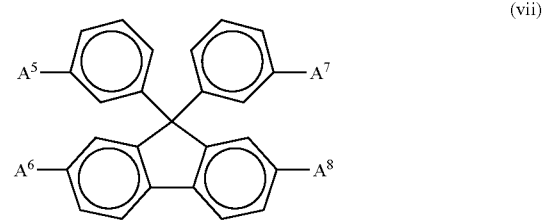

(vii)

wherein $A^5$ to $A^8$ are independently a substituted or unsubstituted biphenyl group or a substituted or unsubstituted naphthyl group.

Fused ring-containing compounds represented by the following formula (viii):

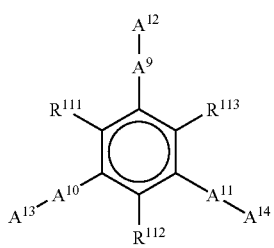

wherein $A^9$ to $A^{14}$ are the same as the above-described ones and $R^{111}$ to $R^{113}$ are independently a hydrogen atom, alkyl group having 1 to 6 carbon atoms, cycloalkyl group having 3 to 6 carbon atoms, alkoxyl group having 1 to 6 carbon atoms, aryloxy group having 5 to 18 carbon atoms, aralkyloxy group having 7 to 18 carbon atoms, arylamino group having 5 to 16 carbon atoms, nitro group, cyano group, ester group having 1 to 6 carbon atoms, or a halogen atom, provided that at least one of $A^9$ to $A^{14}$ is a group having a fused aromatic ring with three or more rings.

Fluorene compounds represented by the following formula (ix):

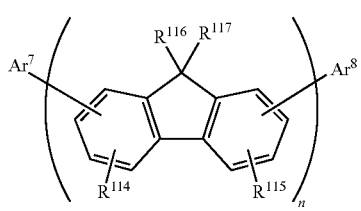

wherein $R^{114}$ and $R^{115}$ are a hydrogen atom, a substituted or unsubstituted alkyl group, substituted or unsubstituted aralkyl group, substituted or unsubstituted aryl group, substituted or unsubstituted heterocyclic group, substituted amino group, cyano group, or a halogen atom; $R^{114}$s bonded to different fluorene groups may be the same or different; and $R^{114}$ and $R^{115}$ bonded to a single fluorene group may be the same or different; $R^{116}$ and $R^{117}$ are a hydrogen atom, a substituted or unsubstituted alkyl group, substituted or unsubstituted aralkyl group, substituted or unsubstituted aryl group, or substituted or unsubstituted heterocyclic group, provided that $R^{116}$s or $R^{117}$s bonded to different fluorene groups may be the same or different; and $R^{116}$ and $R^{117}$ bonded to a single fluorene group may be the same or different: $Ar^7$ and $Ar^8$ are a substituted or unsubstituted fused polycyclic aromatic group with a total number of benzene rings of three or more or a substituted or unsubstituted fused polycyclic heterocyclic group which is bonded to the fluorene group at carbon and has a total number of benzene rings and heterocyclic rings of three or more, provided that $Ar^7$ and $Ar^8$ may be the same or different: and n is an integer of 1 to 10.

Among the above compounds, the host material is preferably the anthracene derivative, more preferably the monoanthracene derivative, and particularly preferably the asymmetrical anthracene.

Phosphorescent compounds can be used as an emitting material. When using a phosphorescent compound, compounds containing a carbazole ring are preferred for a host material. A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable.

The compounds containing a carbazole ring, which are a host suitable for phosphorescent emission, is a compound which allows a phosphorescent compound to emit as a result of energy transfer from its excited state to the phosphorescent compound. The host compound is not limited so long as the compound can transfer its excited energy to a phosphorescent compound and it can be selected depending on purposes. The host compound may contain any heterocyclic ring other than a carbazole ring.

Specific examples of such host compounds include carbazole derivatives, triazole derivatives, oxazole derivatives, oxadiazole derivatives, imidazole derivatives, polyarylalkane derivatives, pyrazoline derivatives, pyrazolone derivatives, phenylene diamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine derivatives, styrylamine derivatives, aromatic dimethylidene-based compounds, porphyrin-based compounds, anthraquinodimethane derivatives, anthrone derivatives, diphenylquinone derivatives, thiopyrane dioxide derivatives, carbodimide derivatives, fluorenylidenemethane derivatives, distyrylpyrazine derivatives; heterocyclic tetracarboxylic anhydrides of naphthalene perylene or the like; naphthaperylene derivatives; various metal complex polysilane-based compounds, the representative examples of which include a metal complex of phthalocyanine derivatives or 8-quinolinol derivatives, metal phthalocyanine, a metal complex having benzoxazole or benzothiazole as a ligand; conductive high-molecular oligomers such as poly (N-vinilcarbazole) derivatives, aniline-based copolymers, thiophene oligomers and polythiophene; and polymer compounds such as polythiophene derivatives, polyphenylene derivatives, polyphenylene vinylene derivatives and polyfluorene derivatives. The host compounds may be used either singly or in combination of two or more.

Specific examples of the host compound are given below.

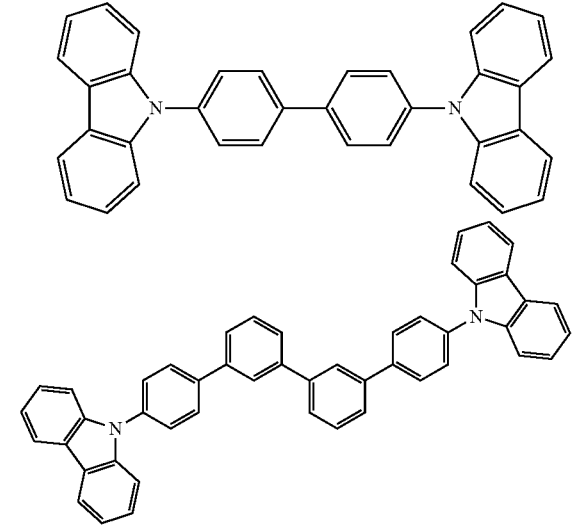

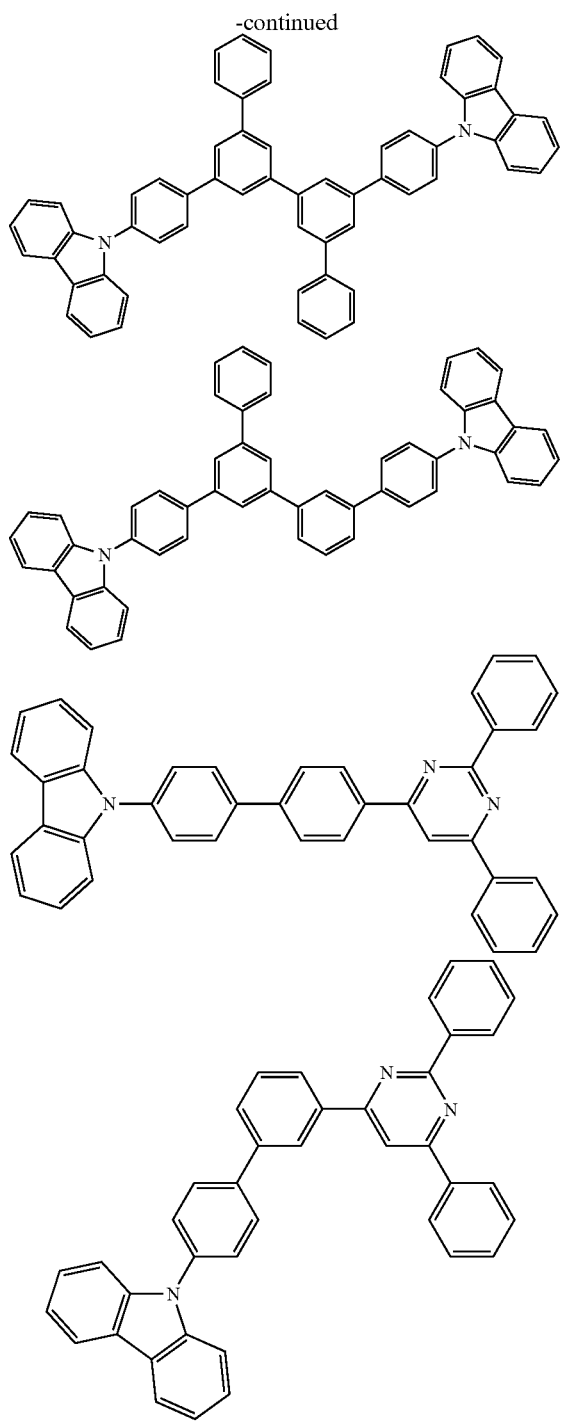

A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable. As a porphyrin metal complex, a porphyrin platinum complex is preferable. The phosphorescent compounds can be used independently or as a combination of two or more kinds.

There are various ligands forming an ortho-metalated metal complex. Preferable ligands include 2-phenylpyridine, 7,8-benzoquinoline, 2-(2-thienyl)pyridine, 2-(1-naphthyl) pyridine and 2-phenylquinoline derivatives. These derivatives may have substituents, if necessary. Fluorides and derivatives with a trifluoromethyl group introduced are particularly preferable as a blue dopant. As an auxiliary ligand, ligands other than the above-mentioned ligands, such as acetylacetonate and picric acid, may be contained.

The content of a phosphorescent dopant in an emitting layer is not limited and can be properly selected according to purposes; for example, it is 0.1 to 70 mass %, preferably 1 to 30 mass %. When the content of a phosphorescent compound is less than 0.1 mass %, emission may be weak and the advantages thereof may not be sufficiently obtained. When the content exceeds 70 mass %, the phenomenon called concentration quenching may significantly proceed, thereby degrading the device performance.

The emitting layer may contain hole-transporting materials, electron-transporting materials and polymer binders, if necessary.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

(Hole-Transporting:Hole-Injecting Layer)

The hole-transporting layer is a layer for helping the injection of holes into the emitting layer so as to transport holes to an emitting region. The hole mobility thereof is large and the ionization energy thereof is usually as small as 5.5 eV or less. Such a hole-transporting layer is preferably made of a material which can transport holes to the emitting layer at a lower electric field intensity. Further, it is preferred that the hole-transporting layer have a hole mobility of at least $10^{-4}$ cm$^2$/V·sec when an electric field of $10^4$ to $10^6$V/cm is applied, for example.

Specific examples of materials for a hole-transporting layer include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylene diamine derivatives (see U.S. Pat. No. 3,615,404, JP-B-51-10105, 46-3712 and 47-25336, and JP-A-54-119925, and others), arylamine derivatives (see U.S. Pat. Nos. 3,567,450, 3,240,597, 3,658,520, 4,232,103, 4,175,961 and 4,012,376, JP-B-49-35702 and 39-27577, JP-A-55-144250, 56-119132 and 56-22437, DE1,110,518, and others), amino-substituted chalcone derivatives (see U.S. Pat. No. 3,526,501, and others), oxazole derivatives (ones disclosed in U.S. Pat. No. 3,257,203, and others), styrylanthracene derivatives (see JP-A-56-46234, and others), fluorenone derivatives (JP-A-54-110837, and others), hydrazone derivatives (see U.S. Pat. No. 3,717,462, JP-A-54-59143, 55-52063, 55-52064, 55-46760, 57-11350, 57-148749 and 2-311591, and others), stilbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), aniline copolymers (JP-A-2-282263), and electroconductive high molecular oligomers (in particular thiophene oligomers).

In addition to the hole-transporting layer, in order to help the injection of holes, it is preferred that the hole-injecting layer be provided separately. As the material for the hole-injecting layer, the organic EL material of the invention may be used singly or in combination with other materials. As the other materials, the same materials as used for the hole-transporting layer or the compounds exemplified by the above-mentioned formula (IV) can be used. The following can also be used: porphyrin compounds (disclosed in JP-A-63-295695 and others), and aromatic tertiary amine compounds and styrylamine compounds (see U.S. Pat. No. 4,127,412, JP-A-53-27033, 54-58445, 55-79450, 55-144250, 56-119132, 61-295558, 61-98353 and 63-295695, and others).

The following can also be given as examples: 4,4'-bis(N-(1-naphthyl)-N-phenylamino)biphenyl (NPD), which has in the molecule thereof two fused aromatic rings, disclosed in U.S. Pat. No. 5,061,569, and 4,4',4"-tris(N-(3-methylphenyl)-N-phenylamino)triphenylamine (MTDATA), wherein three triphenylamine units are linked in a star-burst form, disclosed in JP-A-4-308688.

Inorganic compounds such as p-type Si and p-type SiC as well as aromatic dimethylidene type compounds can also be used as the material of the hole-injecting layer.

The hole-injecting layer or the hole-transporting layer can be formed from the above-mentioned compounds by a known method such as vapor vacuum deposition, spin coating, casting or LB technique. The film thickness of the hole-injecting layer and hole-transporting layer is not particularly limited, and is usually from 1 nm to 5 µm. The hole-injecting layer or hole-transporting layer may be a single layer made of one, or two or more of the above-mentioned materials, or may be stacked hole-injecting layers or hole-transporting layers made of different compounds, insofar as the compound of the invention is contained in a hole-transporting zone.

An organic semiconductor layer is one type of a hole-transporting layer for helping the injection of holes or electrons into an emitting layer, and is preferably a layer having an electric conductivity of $10^{-10}$ S/cm or more. As the material of such an organic semiconductor layer, electroconductive oligomers such as thiophene-containing oligomers or arylamine-containing oligomers disclosed in JP-A-8-193191, and electroconductive dendrimers such as arylamine-containing dendrimers may be used.

(Electron-Injecting/Transporting Layer)

The electron-injecting/transporting layer is a layer which assists injection of electrons into the emitting layer and transports electrons to the emitting region, and exhibits a high electron mobility. An adhesion-improving layer is formed of a material which exhibits excellent adhesion to the cathode among the electron-injecting layers.

The thickness of the electron-transporting layer is arbitrarily selected in the range of several nanometers to several micrometers. When the electron-transporting layer has a large thickness, it is preferable that the electron mobility be at least $10^{-6}$ cm$^2$/Vs or more at an applied electric field of $10^4$ to $10^6$ V/cm in order to prevent an increase in voltage.

The material used in the electron-injecting layer is preferably a metal complex of 8-hydroxyquinoline or a derivative thereof or an oxidiazole derivative. As specific examples of the above-mentioned metal complex of 8-hydroxyquinoline or the derivative thereof, metal chelate oxinoid compounds including a chelate of oxine (8-quinolinol or 8-hydroxyquinoline), for example, tris(8-quinolinol)aluminum, can be given as an electron-injecting material.

An electron-transporting compound of the following general formula can be given as the oxadiazole derivative.

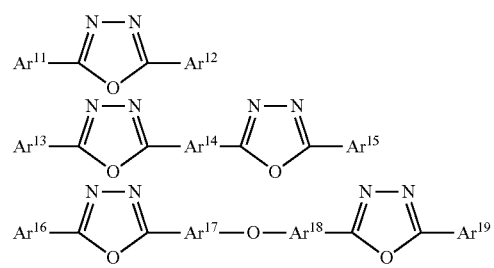

wherein $Ar^{11}$, $Ar^{12}$, $Ar^{13}$, $Ar^{15}$, $Ar^{16}$, and $Ar^{19}$ which may be the same or different, are independently substituted or unsubstituted aryl groups; and $Ar^{14}$, $Ar^{17}$, and $Ar^{18}$, which may be the same or different, are independently substituted or unsubstituted arylene groups.

As examples of the aryl group, a phenyl group, a biphenyl group, an anthryl group, a perylenyl group, and a pyrenyl group can be given. As examples of the arylene group, a phenylene group, a naphthylene group, a biphenylene group, an anthrylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron-transporting compound is preferably one from which a thin film can be formed.

The following compounds can be given as specific examples of the electron-transporting compound.

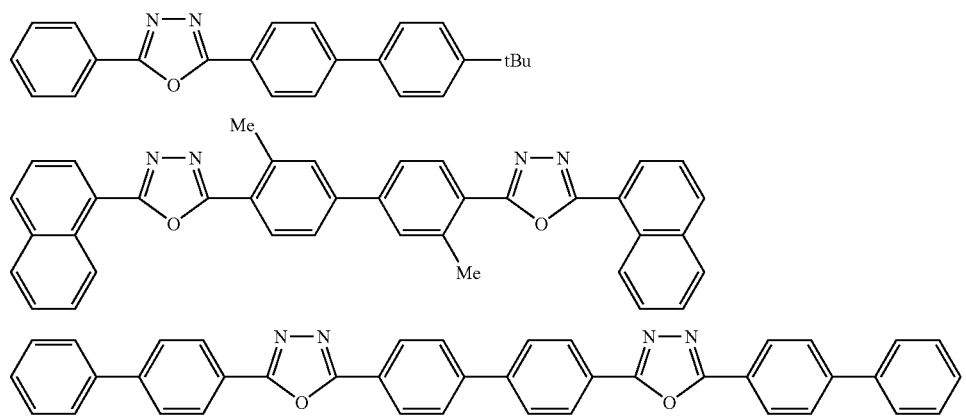

-continued

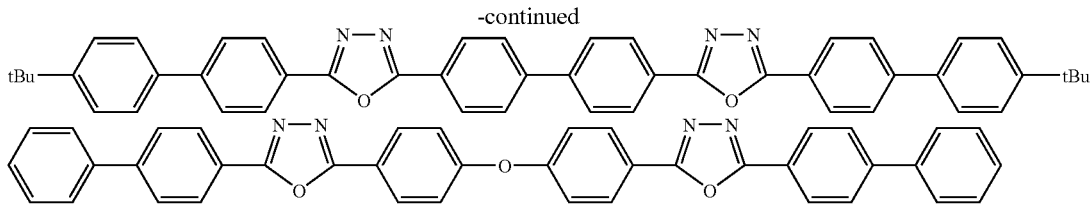

Furthermore, as materials used for the electron-injecting layer and electron-transporting layer, the compounds represented by the following formulas (A) to (F) may be used.

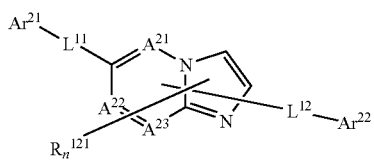     (A)

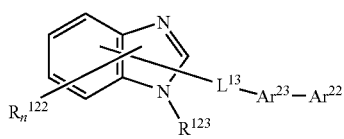     (B)

Nitrogen-containing heterocyclic ring derivatives represented by the formulas (A) and (B) wherein $A^{21}$ to $A^{23}$ are each independently a nitrogen atom or a carbon atom;

$Ar^{21}$ is a substituted or unsubstituted aryl group having 6 to 60 ring carbon atoms or a substituted or unsubstituted heteroaryl group having 3 to 60 ring carbon atoms; $Ar^{22}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms; provided that one of $Ar^{21}$ and $Ar^{22}$ is a substituted or unsubstituted fused ring group having 10 to 60 ring carbon atoms, or a substituted or unsubstituted monohetero fused ring group having 3 to 60 ring carbon atoms;

$Ar^{23}$ is a substituted or unsubstituted arylene group having 6 to 60 ring carbon atoms or a substituted or unsubstituted heteroarylene group having 3 to 60 carbon atoms;

$L^{11}$, $L^{12}$, and $L^{13}$ are independently a single bond, a substituted or unsubstituted arylene group having 6 to 60 ring carbon atoms, a substituted or unsubstituted heteroarylene group having 3 to 60 ring carbon atoms or a substituted or unsubstituted fluorenylene group;

$R^{121}$ and $R^{122}$ are independently a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms, and n is an integer of 0 to 5, provided that, when n is an integer of 2 or more, a plurality of $R^{121}$s and $R^{122}$s may be the same or different; adjacent $R^{121}$s and $R^{122}$s may be bonded to form a carbocyclic aliphatic ring or a carbocyclic aromatic ring;

$R^{123}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms or -$L^{11}$-$Ar^{21}$—$Ar^{22}$.

$$HAr-L^{14}-Ar^{24}—Ar^{25} \quad (C)$$

Nitrogen-containing heterocyclic ring derivatives represented by the formula (C) wherein HAr is a nitrogen-containing heterocyclic ring with 3 to 40 carbon atoms which may have a substituent; $L^{14}$ is a single bond, an arylene group with 6 to 60 carbon atoms which may have a substituent, a heteroarylene group with 3 to 60 carbon atoms which may have a substituent or a fluorenylene group which may have a substituent; $Ar^{24}$ is a divalent aromatic hydrocarbon group with 6 to 60 carbon atoms which may have a substituent; and $Ar^{25}$ is an aryl group with 6 to 60 carbon atoms which may have a substituent or a heteroaryl group with 3 to 60 carbon atoms which may have a substituent.

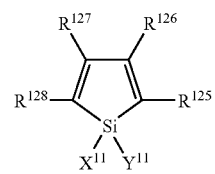     (D)

Silacyclopentadiene derivatives represented by the formula (D) wherein $X^{11}$ and $Y^{11}$ are independently a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted hetero ring, or $X^{11}$ and $Y^{11}$ are bonded to form a saturated or unsaturated ring, and $R^{125}$ to $R^{128}$ are independently a hydrogen atom, a halogen atom, a substituted or unsubstituted aryl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or adjacent groups of $R^{125}$ to $R^{128}$ form a substituted or unsubstituted fused ring.

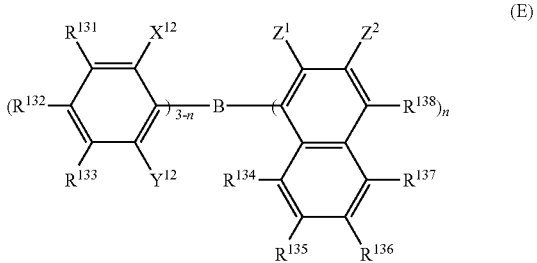
(E)

Borane derivatives represented by the formula (E) wherein $R^{131}$ to $R^{138}$ and $Z^2$ are independently a hydrogen atom, a saturated or unsaturated hydrocarbon group, an aromatic group, a heterocyclic group, a substituted amino group, a substituted boryl group, an alkoxy group, or an aryloxy group, $X^{12}$, $Y^{12}$, and $Z^1$ are independently a saturated or unsaturated hydrocarbon group, an aromatic group, a heterocyclic group, a substituted amino group, an alkoxy group, or an aryloxy group, the substituents for $Z^1$ and $Z^2$ may be bonded together to form a fused ring, n is an integer of 1 to 3, provided that the $Z^1$s may differ when n is 2 or more, and a case in which n is 1, $X^{12}$, $Y^{12}$, and $R^{132}$ are methyl groups, and $R^{138}$ is a hydrogen atom or a substituted boryl group, and a case in which n is 3 and $Z^1$ is a methyl group are excluded.

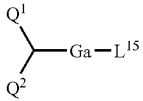
(F)

wherein $Q^1$ and $Q^2$ are independently ligands represented by the following formula (G) and $L^{15}$ is a halogen atom, a substituted or unsubstituted alkyl group, a substituted or unsubstituted cycloalkyl group, a substituted or unsubstituted aryl group, a substituted or unsubstituted heterocyclic group, —OR' (R' is a hydrogen atom, a substituted or unsubstituted alkyl group, a substituted or unsubstituted cycloalkyl group, a substituted or unsubstituted aryl group, or a substituted or unsubstituted heterocyclic group) or a ligand represented by —O-Ga-$Q^3(Q^4)$ ($Q^3$ and $Q^4$ have the same meanings as $Q^1$ and $Q^2$).

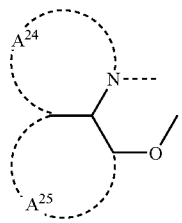
(G)

wherein rings $A^{24}$ and $A^{25}$ are independently a 6-membered aryl ring structure which may have a substituent, and are fused to each other.

The metal complexes have the strong nature of an n-type semiconductor and large ability of injecting electrons. Further, the energy generated at the time of forming a complex is small so that a metal is then strongly bonded to ligands in the complex formed and the fluorescent quantum efficiency becomes large as the emitting material.

Specific examples of the substituents for the rings $A^{24}$ and $A^{25}$ forming the ligand of the above formula (G) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, substituted or unsubstituted aryl groups such as a phenyl group, naphthyl group, 3-methylphenyl group, 3-methoxyphenyl group, 3-fluorophenyl group, 3-trichloromethylphenyl group, 3-trifluoromethylphenyl group, and 3-nitrophenyl group, substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, substituted or unsubstituted aryloxy groups such as a phenoxy group, p-nitrophenoxy group, p-tert-butylphenoxy group, 3-fluorophenoxy group, pentafluorophenyl group, and 3-trifluoromethylphenoxy group, substituted or unsubstituted alkylthio groups such as a methylthio group, ethylthio group, tert-butylthio group, hexylthio group, octylthio group, and trifluoromethylthio group, substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, diethylamino group, ethylamino group, diethylamino group, dipropylamino group, dibutylamino group, and diphenylamino group, acylamino groups such as a bis(acetoxymethyl)amino group, bis(acetoxyethyl)amino group, bis(acetoxypropyl) amino group, and bis(acetoxybutyl)amino group, a hydroxyl group, a siloxy group, an acyl group, a substituted or unsubstituted carbamoyl groups such as a carbamoyl group, a methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imide group, cycloalkyl groups such as a cyclopentane group and a cyclohexyl group, aryl groups such as a phenyl group, naphthyl group, biphenyl group, anthryl group, phenanthryl group, fluorenyl group, and pyrenyl group, heterocyclic groups such as a pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, triathinyl group, carbazolyl group, furanyl group, thiophenyl group, oxazolyl group, oxadiazolyl group, benzooxazolyl group, thiazolyl group, thiadiazolyl group, benzothiazolyl group, triazolyl group, imidazolyl group, and benzimidazolyl group, and the like. The above substituents may be bonded to form a six-membered aryl ring or heterocyclic ring.

A preferred embodiment of the invention is a device containing a reducing dopant in an electron-transferring region or in an interfacial region between the cathode and the organic layer. The reducing dopant is defined as a substance which can reduce an electron-transferring compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal organic complexes, alkaline earth metal organic complexes, and rare earth metal organic complexes.

More specific examples of the preferred reducing dopants include at least one alkali metal selected from the group consisting of Li (work function: 2.9 eV), Na (work function: 2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV). Dopants having a work function of 2.9 eV or less are particularly preferable.

Among these, a more preferable reducing dopant is at least one alkali metal selected from the group consisting of K, Rb and Cs. Even more preferable is Rb or Cs. Most preferable is Cs.

These alkali metals are particularly high in reducing ability. Thus, the addition of a relatively small amount thereof to an electron-injecting zone improves the luminance of the organic EL device and make the lifetime thereof long. As a reducing agent having a work function of 2.9 eV or less, combinations of two or more alkali metals are preferable, particularly combinations including Cs, such as Cs and Na, Cs and K, Cs and Rb, or Cs, Na and K are preferable.

The combination containing Cs makes it possible to exhibit the reducing ability efficiently. The luminance of the organic EL device can be improved and the lifetime thereof can be made long by the addition thereof to its electron-injecting zone.

In the invention, an electron-injecting layer made of an insulator or a semiconductor may further be provided between a cathode and an organic layer. By forming the electron-injecting layer, a current leakage can be effectively prevented and electron-injecting properties can be improved.

As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, electron-injecting properties can be preferably further improved.

Specifically preferable alkali metal calcogenides include $Li_2O$, LiO, $Na_2S$, $Na_2Se$ and NaO and preferable alkaline earth metal calcogenides include CaO, BaO, SrO, BeO, BaS and CaSe. Preferable halides of alkali metals include LiF, NaF, KF, LiCl, KCl and NaCl. Preferable halides of alkaline earth metals include fluorides such as $CaF_2$, $BaF_2$, $SrF_2$, $MgF_2$ and $BeF_2$ and halides other than fluorides.

Semiconductors forming an electron-transporting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn.

An inorganic compound forming an electron-transporting layer is preferably a microcrystalline or amorphous insulating thin film. When the electron-transporting layer is formed of the insulating thin films, more uniformed thin film is formed, whereby pixel defects such as a dark spot are decreased.

Examples of such an inorganic compound include the above-mentioned alkali metal calcogenides, alkaline earth metal calcogenides, halides of alkali metals, and halides of alkaline earth metals.

(Cathode)

For the cathode, the following may be used: an electrode substance made of a metal, an alloy or an electroconductive compound, or a mixture thereof which has a small work function (for example, 4 eV or less). Specific examples of the electrode substance include sodium, sodium-potassium alloy, magnesium, lithium, magnesium/silver alloy, aluminum/aluminum oxide, aluminum/lithium alloy, indium, and rare earth metals.

This cathode can be formed by making the electrode substances into a thin film by vapor deposition, sputtering or some other method.

In the case where light is emitted from the emitting layer through the cathode, the cathode preferably has a light transmittance of larger than 10%.

The sheet resistance of the cathode is preferably several hundred $\Omega/\square$ or less, and the film thickness thereof is usually from 10 nm to 1 µm, preferably from 50 to 200 nm.

(Insulating Layer)

In the organic EL device, pixel defects based on leakage or a short circuit are easily generated since an electric field is applied to the ultrathin film. In order to prevent this, it is preferred to insert an insulative thin layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, cesium fluoride, cesium carbonate, aluminum nitride, titanium oxide, silicon oxide, germanium oxide, silicon nitride, boron nitride, molybdenum oxide, ruthenium oxide, and vanadium oxide.

A mixture or laminate thereof may be used.

(Example of Fabricating Organic EL Device)

Using the above-mentioned materials, an organic EL device can be fabricated by forming an anode, a hole-injecting layer, a hole-transporting layer, an emitting layer, an electron-injecting layer or the like, followed by formation of a cathode. The organic EL device can be also fabricated in the order reverse to the above, i.e., the order from a cathode to an anode.

An example of the fabrication of the organic EL device will be described below which has a structure wherein the following are successively formed on a transparent substrate: anode/hole-injecting layer/hole-transporting layer/emitting layer/electron-transporting layer/cathode.

First, a thin film made of an anode material is formed into a thickness of 1 µm or less, preferably 10 to 200 nm on an appropriate transparent substrate by vapor deposition, sputtering or some other method, thereby forming an anode.

Next, a hole-injecting layer and a hole-transporting layer are formed on this anode. These layers can be formed by vacuum deposition, spin coating, casting, LB technique, or some other method. Vacuum deposition is preferred since a homogenous film is easily obtained and pinholes are not easily generated.

In the case where the hole-injecting layer and the hole-transporting layer are formed by vacuum vapor deposition, conditions for the deposition vary depending upon the compound used, the desired crystal structure or recombining structure of the hole-injecting layer and the hole-transporting layer, and others. In general, the conditions are preferably selected from the following: deposition source temperature of 50 to 450° C., vacuum degree of $10^{-7}$ to $10^{-3}$ torr, vapor deposition rate of 0.01 to 50 nm/second, substrate temperature of −50 to 300° C., and film thickness of 5 nm to 5 µm.

Next, an emitting layer is formed on the hole-transporting layer. The emitting layer can also be formed by making a desired organic luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vacuum vapor deposition, conditions for the deposition, which vary depending on a compound used, can be generally selected from conditions similar to those for the hole-transporting layer.

Next, an electron-transporting layer is formed on this emitting layer. Like the hole-transporting layer and the emitting layer, the layer is preferably formed by vacuum vapor deposition because a homogenous film is required. Conditions for the deposition can be selected from conditions similar to those for the hole-transporting layer and the emitting layer.

Lastly, a cathode is stacked thereon to obtain an organic EL device.

The cathode is made of a metal, and vapor deposition or sputtering may be used. However, vapor vacuum deposition is preferred in order to protect underlying organic layers from being damaged when the cathode film is formed.

For the organic EL device fabrication that has been described above, it is preferred that the formation from the anode to the cathode is continuously carried out, using only one vacuuming operation.

The method for forming each of the layers in the organic EL device of the invention is not particularly limited. Specifically the layers can be formed by a known method, such as vacuum deposition, molecular beam deposition (MBE method), or coating method such as dipping, spin coating, casting, bar coating and roll coating using a solution obtained by dissolving materials in a solvent.

The film thickness of each of the organic layers in the organic EL device of the invention is not particularly limited. In general, defects such as pinholes are easily generated when the film thickness is too small. Conversely, when the film thickness is too large, a high applied voltage becomes necessary, leading to low efficiency. Usually, the film thickness is preferably in the range of several nanometers to one micrometer.

The organic EL device emits light when applying a voltage between electrodes. If a DC voltage is applied to the organic EL device, emission can be observed when the polarities of the anode and the cathode are positive and negative, respectively, and a DC voltage of 5 to 40 V is applied. When a voltage with an opposite polarity is applied, no electric current flows and hence, emission does not occur. If an AC voltage is applied, uniform emission can be observed only when the cathode and the anode have a positive polarity and a negative polarity, respectively. The waveform of the AC applied may be arbitrary.

EXAMPLES

The material for an organic EL device and the organic EL device of the invention will be described hereinbelow in detail with reference to Examples, which should not be construed as limiting the scope of the invention.

Example 1

[Synthesis of a Compound Shown by the Formula (B-8)]

The compound shown by the formula (B-8) was synthesized according to the following synthesis scheme.

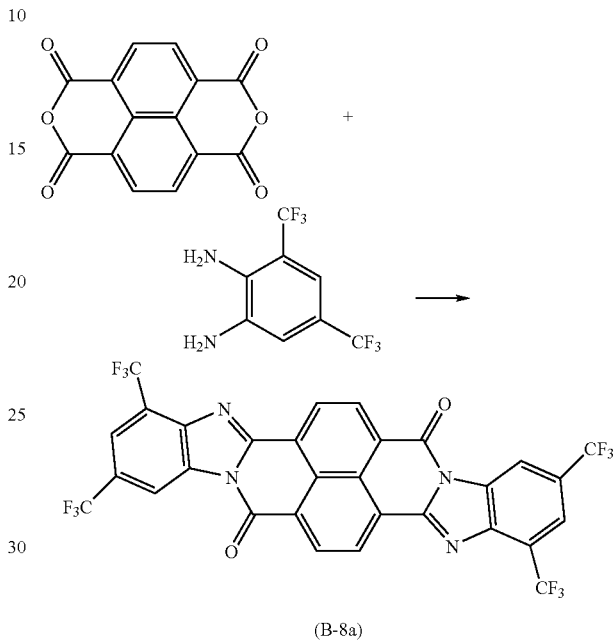

(B-8a)

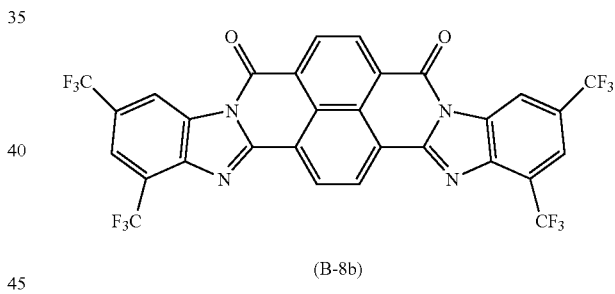

(B-8b)

In the above-mentioned synthesis scheme, a mixture of a compound shown by the formula (B-8a), a compound shown by the formula (B-8b) and a plurality of isomers which differ from these compounds in the trifluoromethyl group substituting position is obtained. Hereinafter, this isomer mixture is referred to as (B-8).

3.0 g of naphthalenetetracarboxylic anhydride and 5.4 g of 1,2-diamino-3,5-trifluorobenzene were put in 30 ml of acetic acid, and stirred under reflux for 5 hours. After allowing the mixture to cool, deposited orange crystals were filtered out, and washed with acetonitrile and ethanol. The crystals were purified by sublimation, whereby 5.2 g of an orange solid was obtained.

The mass spectroscopy of this compound confirmed a peak at M/Z=684.

This compound was dissolved in acetonitrile in a concentration of 0.01 mol/l. The reduction potential was measured by cyclic voltammetry using tetrabutylammonium perchlorate (TBAP) as a supporting electrolyte, a glassy carbon electrode as a working electrode, a platinum electrode as a counter electrode, a silver-silver chloride electrode as a reference electrode. The reduction potential of the compound (B-8) at a sweep rate of 0.1 V/s was −0.3V. The reduction potential of ferrocene (hereinafter referred to as Fc) as the reference material was measured in the same manner as mentioned above, and the first oxidation potential thereof was found to be 0.5V. When the oxidation potential of ferrocene is taken as a standard, the reduction potential of the compound (B-8) was −0.8V (vs F$^+$/Fc).

Example 2

[Synthesis of a Compound Shown by the Formula (A-3)]

A compound shown by the formula (A-3) was synthesized according to the following synthesis scheme.

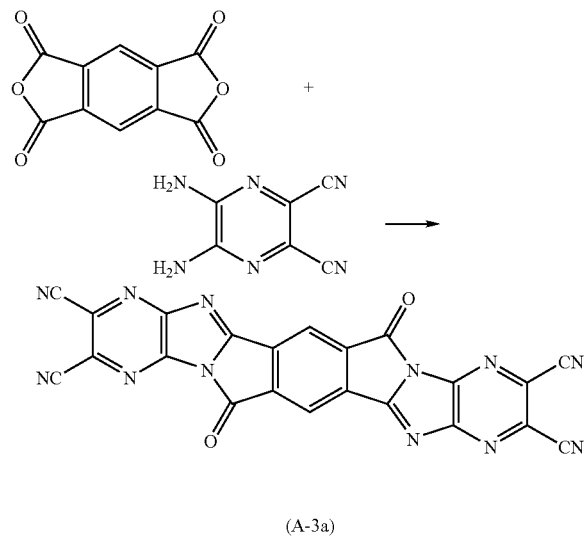

(A-3a)

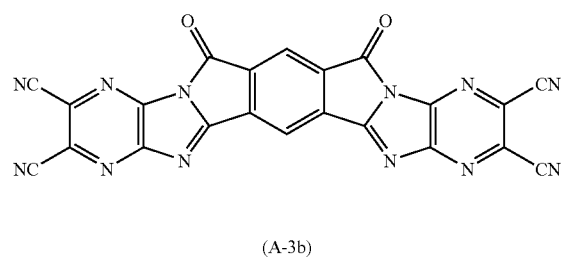

(A-3b)

In the above-mentioned synthesis scheme, a mixture of a compound shown by the formula (A-3a) and a compound shown by the formula (A-3b) can be obtained. Hereinafter, this isomer mixture is referred to as (A-3).

2.4 g of pyromellitic anhydride and 3.5 g of 5,6-diamino-2,3-dicyanopyrazine were added to 50 ml of pyridine, and the resulting mixture was stirred under reflux for 12 hours. After allowing the mixture to cool, deposited white crystals were filtered out, and washed with acetonitrile and ethanol. The crystals were purified by sublimation, whereby 1.5 g of an orange solid was obtained.

The mass spectroscopy of this compound confirmed a peak at M/Z=466.

The reduction potential was measured by cyclic voltammetry in the same manner as in Example 1. When the first oxidation potential of ferrocene (hereinafter referred to as Fc) as the reference material is taken as a standard, the reduction potential of the compound (A-3) was −0.6V (vs Fc+/Fc).

Example 3

[Synthesis of a Compound Shown by the Formula (C-3)]

A compound shown by the formula (C-3) was synthesized according to the following synthesis scheme.

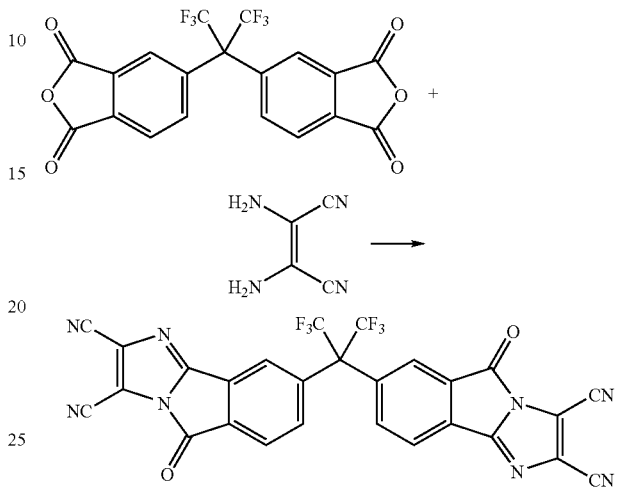

4.9 g of 4,4'-(hexafluoroisopropylidene)diphthalic anhydride and 3.6 g of diaminomalononitrile were put in 50 ml of acetic acid, and the resulting mixture was stirred under reflux for 3 hours. After allowing the mixture to cool, deposited crystals were filtered out, and washed with acetonitrile and ethanol. The crystals were purified by sublimation, whereby 2.4 g of a white solid was obtained.

The mass spectroscopy of this compound confirmed a peak at M/Z=588.

The reduction potential was measured by cyclic voltammetry in the same manner as in Example 1. When the first oxidation potential of ferrocene (hereinafter referred to as Fc) as the reference material is taken as a standard, the reduction potential of the compound (C-3) was ±0.9V (vs Fc+/Fc).

Example 4

[Synthesis of a Compound Shown by the Formula (P-1)]

A compound shown by the formula (P-1) was synthesized according to the following synthesis scheme.

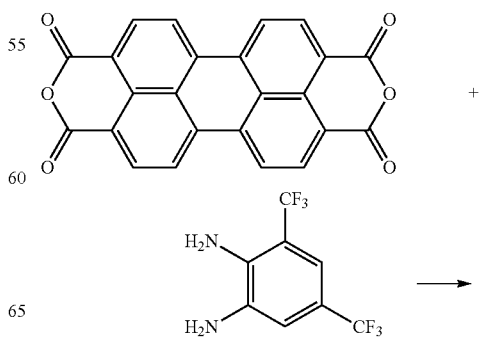

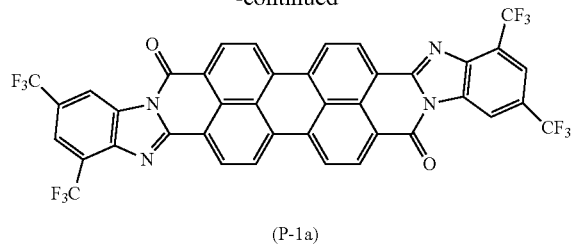

(P-1a)

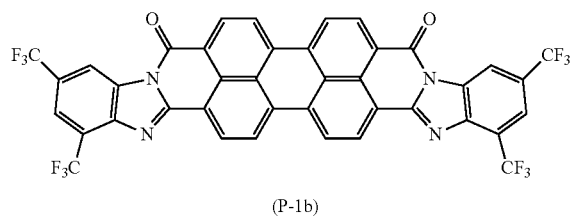

(P-1b)

In the above-mentioned synthesis scheme, a mixture of a compound shown by the formula (P-1a), a compound shown by the formula (P-1b) and a plurality of isomers which differ from these compounds in the trifluoromethyl group substituting position is obtained. Hereinafter, this isomer mixture is referred to as (P-1).

3.9 g of 3,4,9,10-perylenetetracarboxylic anhydride and 6.1 g of 1,2-diamino-3,5-trifluorobenzene were put in 130 ml of 1-methyl-2-pyrrolidone, and the resulting mixture was stirred under reflux for 10 hours. After allowing the mixture to cool, deposited crystals were filtered out, and washed with N,N-dimethylformamide (DMF) and ethanol. The crystals were purified by sublimation, whereby 2.7 g of reddish purple crystals were obtained.

The mass spectroscopy of this compound confirmed a peak at M/Z=808.

The reduction potential was measured by cyclic voltammetry in the same manner as in Example 1. When the first oxidation potential of ferrocene (hereinafter referred to as Fc) as the reference material is taken as a standard, the reduction potential of the compound (P-1) was ±0.7V (vs Fc+/Fc).

[Organic EL Device]

Example 5

A glass substrate of 25 mm by 75 mm by 1.1 mm thick with an ITO transparent electrode (GEOMATEC CO., LTD.) was subjected to ultrasonic cleaning with isopropyl alcohol for 5 minutes, and cleaned with ultraviolet rays and ozone for 30 minutes.

The cleaned glass substrate having the transparent electrode lines was then secured to a substrate holder of an apparatus for vapor vacuum deposition. First, the compound shown by the formula (B-8) synthesized in Example 1 and a compound represented by the following formula (D-1) were deposited with a thickness of 60 nm onto the surface of the glass substrate on which the transparent electrode lines were formed so as to cover the transparent electrodes such that the amount ratio of the compound (B-8) and the compound (D-1) become 2:98 (molar ratio). The mixture film served as a hole-injecting layer.

Subsequently, a 20 nm-thick film of a compound represented by the following formula (HTM-1) was formed on the above-obtained mixture film. This film functioned as a hole-transporting layer.

Further, a compound EM1 was deposited thereon to form a film (with a thickness of 40 nm). Simultaneously, the following amine compound D1 having a styryl group was deposited as an emitting molecule such that the weight ratio of EM1 and D1 became 40:2. This film functioned as an emitting layer.

An Alq film was deposited on the above-obtained film. The film serves as an electron-injecting layer. Then, Li as a reductive dopant (Li source: manufactured by SAES Getters Co., Ltd.) and Alq were co-deposited, whereby an Alq:Li film (film thickness: 10 nm) was formed as an electron-injecting layer (cathode). Metal aluminum was deposited on the Alq:Li film to form a metallic cathode, whereby an organic EL emitting device was fabricated.

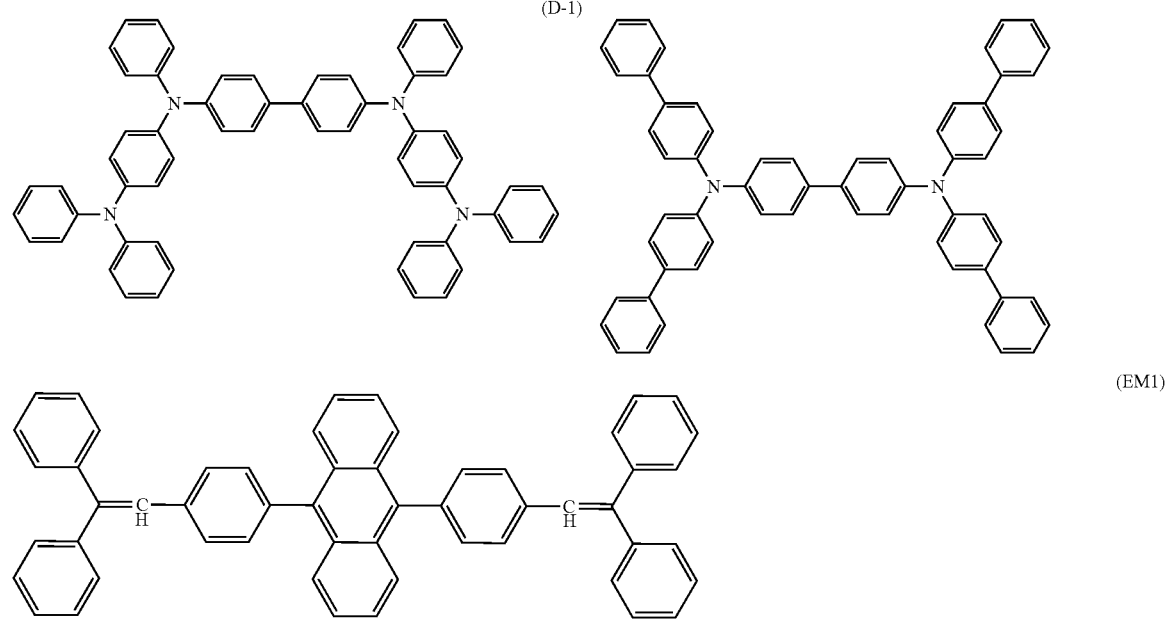

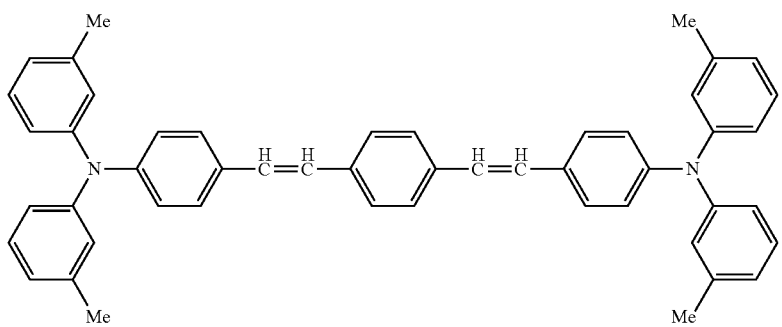

(D1)

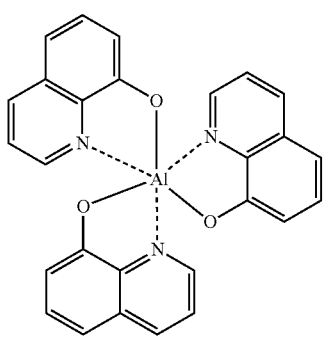

Alq

The organic EL device was evaluated by measuring a driving voltage at a current density of 10 mA/cm² and a half life of luminance at an initial luminance of 1,000 nits, at room temperature, and with a DC constant power supply. The results obtained are shown in Table 1.

Example 6

An organic EL device was fabricated and evaluated in the same manner as in Example 5, except that the compound (B-8) alone was used in the hole-injecting layer and the thickness thereof was changed to 3 nm, and the thickness of the compound (HTM-1) as the hole-transporting layer was changed to 77 nm. The results are shown in Table 1.

Example 7

An organic EL device was fabricated and evaluated in the same manner as in Example 5, except that only the compound (A-3) synthesized in Example 2 was used in the hole-injecting layer and the thickness thereof was changed to 10 nm and the thickness of the compound (HTM-1) as the hole-transporting layer was changed to 70 nm. The results are shown in Table 1.

Example 8

An organic EL device was fabricated and evaluated in the same manner as in Example 6, except that only the compound (C-3) synthesized in Example 3 was used in the hole-injecting layer. The results are shown in Table 1.

Example 9

An organic EL device was fabricated and evaluated in the same manner as in Example 4, except that only the compound (P-1) synthesized in Example 6 was used in the hole-injecting layer. The results are shown in Table 1.

Comparative Example 1

An organic EL device was fabricated and evaluated in the same manner as in Example 5, except that the compound shown by the formula (D-1) alone was deposited in a film to form the hole-injecting layer.
The results are shown in Table 1.

TABLE 1

| | Materials for the hole-injecting layer | Driving voltage (V) | Half life (hr) |
|---|---|---|---|
| Example 5 | Formula (B-8) Formula (D-1) | 6.0 | 7,900 |
| Example 6 | Formula (B-8) | 5.7 | 8,400 |
| Example 7 | Formula (A-3) | 6.2 | 8,500 |
| Example 8 | Formula (C-3) | 6.1 | 7,500 |
| Example 9 | Formula (P-1) | 5.6 | 8,200 |
| Com. Exam. 1 | Formula (D-1) | 6.6 | 5,000 |

INDUSTRIAL APPLICABILITY

The material for an organic EL device of the invention is preferable as the constituting material for an organic EL device, in particular, as the material for a hole-transporting layer and a hole-injecting layer. The material for an organic EL device of the invention can also be used as a carrier-transporting material of an electrophotographic photoconductor.

The organic EL device of the invention can be suitably used as a light source such as a planar emitting body and backlight of a display, a display part of a portable phone, PDA, a car navigator, or an instruction panel of an automobile, an illuminator, and the like.

The contents of the above-mentioned documents are herein incorporated by reference in its entirety.

The invention claimed is:
1. A compound shown by the following formula (III):

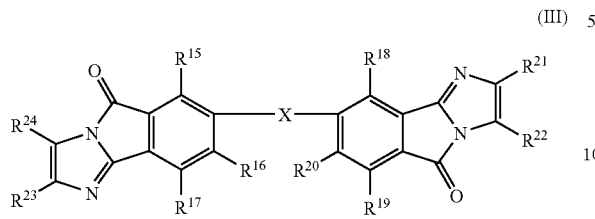

wherein $R^{15}$ to $R^{24}$, which may be the same or different, are a hydrogen atom, a halogen atom, a cyano group, an alkyl group, an aryl group, a fluoroalkyl group, an alkoxy group, an aryloxy group or a heterocyclic ring; adjacent groups of $R^{15}$ to $R^{24}$ may be bonded to form an aromatic ring or a heterocyclic ring, and the aromatic ring or the heterocyclic ring may have a substituent; and X is a single bond, —CO—, —S—, —SO—, —SO$_2$— or —CR$^{25}$R$^{26}$— wherein $R^{25}$ and $R^{26}$ are independently a hydrogen atom, a halogen atom, an alkyl group, an aryl group or a fluoroalkyl group, and $R^{25}$ and $R^{26}$ may be bonded to form a ring.

2. An organic electroluminescence device comprising an anode, a cathode and an organic thin film layer between the anode and the cathode, wherein the organic thin film layer is a stack composed of a hole-injecting layer, a hole-transporting layer, an emitting layer and an electron-transporting layer being stacked sequentially from the anode, and the hole-injecting layer comprises a compound shown by the following formula (III):

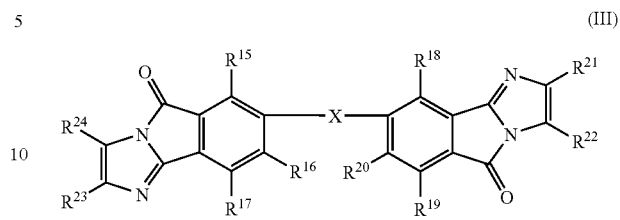

wherein $R^{15}$ to $R^{24}$, which may be the same or different, are a hydrogen atom, a halogen atom, a cyano group, an alkyl group, an aryl group, a fluoroalkyl group, an alkoxy group, an aryloxy group or a heterocyclic ring; adjacent groups of $R^{15}$ to $R^{24}$ may be bonded to form an aromatic ring or a heterocyclic ring, and the aromatic ring or the heterocyclic ring may have a substituent; and X is a single bond, —O—, —CO—, —S—, —SO—, —SO$_2$— or —CR$^{25}$R$^{26}$— wherein $R^{25}$ and $R^{26}$ are independently a hydrogen atom, a halogen atom, an alkyl group, an aryl group or a fluoroalkyl group, and $R^{25}$ and $R^{26}$ may be bonded to form a ring.

3. The device according to claim 2 wherein at least one of $R^{15}$ to $R^{24}$ is a fluorine atom, a fluoroalkyl group or a cyano group.

* * * * *